(12) United States Patent
Garbey et al.

(10) Patent No.: US 10,154,882 B2
(45) Date of Patent: Dec. 18, 2018

(54) GLOBAL LAPAROSCOPY POSITIONING SYSTEMS AND METHODS

(71) Applicants: UNIVERSITY OF HOUSTON, Houston, TX (US); THE METHODIST HOSPITAL, Houston, TX (US)

(72) Inventors: Marc Garbey, Houston, TX (US); Brian James Dunkin, Houston, TX (US); Barbara Lee Bass, Houston, TX (US)

(73) Assignees: UNIVERSITY OF HOUSTON SYSTEM, Houston, TX (US); THE METHODIST HOSPITAL, Houston, TX (US)

( * ) Notice: Subject to any disclaimer, the term of this patent is extended or adjusted under 35 U.S.C. 154(b) by 14 days.

(21) Appl. No.: 14/667,333

(22) Filed: Mar. 24, 2015

(65) Prior Publication Data

US 2015/0265370 A1 Sep. 24, 2015

Related U.S. Application Data

(60) Provisional application No. 61/969,812, filed on Mar. 24, 2014.

(51) Int. Cl.
*A61B 1/32* (2006.01)
*A61B 19/00* (2006.01)
(Continued)

(52) U.S. Cl.
CPC ...... *A61B 19/5244* (2013.01); *A61B 17/3421* (2013.01); *A61B 34/20* (2016.02); *A61B 90/39* (2016.02); *A61B 90/92* (2016.02); *A61B 90/94* (2016.02); *A61B 90/96* (2016.02); *A61B 2034/2057* (2016.02); *A61B 2034/2065* (2016.02); *A61B 2090/3937* (2016.02); *A61B 2090/3983* (2016.02)

(58) Field of Classification Search
CPC . A61B 17/3421–17/3462; A61B 90/90–90/98; A61B 2034/2055–2034/2057; A61B 2034/2065
See application file for complete search history.

(56) References Cited

U.S. PATENT DOCUMENTS 6,527,704 B1 * 3/2003 Chang .................... A61B 1/042
600/112
8,670,816 B2 * 3/2014 Green .................. A61B 8/0841
600/407

(Continued)

FOREIGN PATENT DOCUMENTS

WO WO 2014/089439 6/2014

OTHER PUBLICATIONS

PCT Search Report and Written Opinion issued in International Application No. PCT/US2015/022287, dated Jul. 10, 2015.

*Primary Examiner* — Eduardo C Robert
*Assistant Examiner* — Steven Cotroneo
(74) *Attorney, Agent, or Firm* — Parker Highlander, PLLC

(57) ABSTRACT

Systems and methods for determining a position of a surgical tool. Exemplary embodiments can comprise a surgical port, a reference marker, and a camera mounted to a proximal end of the surgical port and configured to capture image data associated with the reference marker.

15 Claims, 19 Drawing Sheets
(5 of 19 Drawing Sheet(s) Filed in Color)

(51) Int. Cl.
*A61B 17/34* (2006.01)
*A61B 90/96* (2016.01)
*A61B 90/92* (2016.01)
*A61B 90/94* (2016.01)
*A61B 90/00* (2016.01)
*A61B 34/20* (2016.01)

(56) References Cited

U.S. PATENT DOCUMENTS

| | | | |
|---|---|---|---|
| 2007/0034731 A1* | 2/2007 | Falco | G01B 7/008 244/3.1 |
| 2008/0200794 A1* | 8/2008 | Teichman | A61B 34/20 600/407 |
| 2012/0078236 A1* | 3/2012 | Schoepp | A61B 5/061 606/1 |
| 2012/0101508 A1* | 4/2012 | Wook Choi | B25J 9/1697 606/130 |
| 2013/0172907 A1* | 7/2013 | Harris | A61B 19/201 606/130 |
| 2014/0171787 A1* | 6/2014 | Garbey | A61B 5/061 600/424 |

* cited by examiner

| Picture | dx | dy | dθ | dφ |
|---|---|---|---|---|
| 1 | 0.6 | 0.06 | 0.0 | 0.0 |
| 1 | 0.6 | 0.1 | 0.0 | 0.0 |
| 2 | 0.3 | 0.1 | -0.6 | 0.0 |
| 2 | 0.3 | 0.1 | 0.5 | 0.0 |
| 3 | -0.3 | 0.1 | -2.2 | 0.0 |
| 3 | -0.3 | 0.1 | -2.5 | 0.0 |
| 4 | 0.2 | 0.0 | -1.05 | 0.0 |
| 4 | 0.2 | 0.0 | -1.0 | 0.0 |
| 5 | -0.2 | 0.06 | 0.0 | 0.0 |
| 5 | -0.2 | 0.1 | 0.0 | 0.0 |
| 6 | 0.0 | 0.2 | 0.0 | 1.4 |
| 6 | 0.0 | 0.2 | 0.0 | 1.5 |
| 7 | 0.3 | 0.2 | 0.0 | 0.65 |
| 7 | 0.3 | 0.2 | 0.0 | 0.5 |
| 8 | 0.0 | 0.5 | 0.0 | 0.9 |
| 8 | 0.0 | 0.5 | 0.0 | 1.0 |

FIG. 21

GLOBAL LAPAROSCOPY POSITIONING SYSTEMS AND METHODS

CROSS-REFERENCE TO RELATED APPLICATIONS

This application claims priority to U.S. Provisional Patent Application Ser. No. 61/969,812 filed Mar. 24, 2014 and entitled "Global Laparoscopy Positioning Systems and Methods," the entire contents of which are incorporated herein by reference.

TECHNICAL FIELD

Exemplary embodiments of the present disclosure relate to a global positioning system configured to register the position and orientation of surgical tools during laparoscopic procedures utilizing a surgical port.

BACKGROUND

Laparoscopic surgery is a common and popular alternative to open surgery due to the considerable reduction of recovery time, pain and complications. However, many obstacles make the surgeon's work difficult and inefficient, including limited access to the operating field, indirect vision, and operating theaters originally built for open surgery. There has been an interest in the field to develop systems to aid in "operating room awareness." Operating room awareness refers to creating an operating room that can collect data related to the operation in progress and use the data to assist the surgeon and medical staff. There is also interest using the collected data to assist in surgeon and staff training and evaluation.

One component of operating room awareness is tool identification, location and navigation. Historically, surgical tools have been identified and positioned using visual inspection by the surgeon and/or medical staff. Some automated systems exist; however, the accuracy of these systems can be compromised by the presence of metals and fluids in the operating space and the reliance on a constantly-changing point of reference for the tracking device.

Therefore, a need in the art exists for a minimally intrusive, yet robust, system to analyze data generated during a medical procedure and provide real-time context awareness to the surgery team as well as post-procedure evaluation tools.

SUMMARY OF THE INVENTION

Presented are systems and methods directed to a surgical tool positioning and tracking system. Embodiments of the system may include a surgical port, and one or more reference markers, and a camera. Particular embodiments may include a first reference marker positioned at a first fixed location distal to the surgical port. In specific embodiments, the camera may be coupled to the surgical port and configured to capture image data associated with the first reference marker. Certain embodiments may also include tracking elements associated with a surgical tool and a camera. The surgical port may have a proximal end configured to be located outside the body of a patient and a distal end configured to be located within an internal portion of the body of the patient. The surgical port may also have a channel extending between the proximal end and the distal end. The surgical tool may be sized and configured to access the internal portion of the body of the patient through the channel of the surgical port. The reference markers may be located at fixed locations distal to the camera. The tracking elements may be removably coupled to the surgical tool and a camera mounted to the proximal end of the surgical port may be configured to capture image data associated with the tracking element.

In certain embodiments, the first reference marker is positioned in an operating room. In particular embodiments, the first reference marker is positioned on the ceiling of an operating room. In specific embodiments, the first reference marker comprises a plurality of intersecting segments. In particular embodiments, the plurality of intersecting segments forms a cross shape. In certain embodiments, the camera is coupled to the proximal end of the surgical port. Particular embodiments further comprise a second reference marker positioned at a second fixed location distal to the surgical port. In some embodiments, the surgical port is a trocar. In specific embodiments, the trocar comprises a base at the proximal end and a cannula at the distal end, and wherein the camera is mounted to the base.

In certain embodiments, the camera is in a fixed position with respect to the surgical port. In particular embodiments, the camera is movable on the surgical port. In some embodiments, the camera is directed towards the first reference marker, and in specific embodiments, the camera is configured to be directed away from a body of a patient. In certain embodiments, the camera includes a light element for illuminating the first reference marker. In particular embodiments, the camera is in communication with the computer system to transmit the image data to the computer system. Some embodiments further comprise a tracking element coupled to a tool inserted into the surgical port.

In certain embodiments, the tracking element includes at least one of a color, a shape, a pattern, bar code, and a character. Particular embodiments further comprise a surgical tool, where the surgical tool is sized and configured to access the internal portion of the body of the patient through the channel of the surgical port. Specific embodiments further comprise a tracking element coupled to the surgical tool. In certain embodiments, the tracking element corresponds to at least one of an identity of the surgical tool, an orientation of the surgical tool, and a position of the surgical tool. In particular embodiments, the tracking element is positioned at a location proximate a handle associated with the surgical tool. In some embodiments, the camera is further configured to capture image data associated with a surgeon.

Certain embodiments include a method for determining a global position of a surgical tool. In particular embodiments, the method comprises inserting a surgical tool into a surgical port, where the surgical port comprises: a proximal end configured to be located outside a body of a patient; a distal end configured to be located within an internal portion of the body of the patient; a channel extending between the proximal end and the distal end; and a camera coupled to the surgical port. In some embodiments, the method also comprises capturing image data with the camera, wherein the image data is associated with a first reference marker; providing the image data to a processor; and processing the image data to determine global position information associated with the surgical tool.

In specific embodiments, inserting the surgical tool to the surgical port further comprises inserting a portion of the surgical tool into the channel extending between the proximal end and the distal end of the surgical port. In certain embodiments, the surgical tool comprises a tracking element, and the image data is also associated with the tracking element. Some embodiments further comprise processing the image data to determine tracking information associated with the surgical tool. In specific embodiments, the tracking information includes at least one of an orientation of the surgical tool and a position of the surgical tool.

Embodiments of the present invention provide spatial localization of laparoscopy tool. Certain embodiments comprise: (a) computation of the position of the tip of the laparoscopic tool in trocar coordinate; and (b) computation of the position of the trocar position in the operating room coordinates. The combination of (a) and (b) provides a solution to localize the position of the tool.

In certain embodiments, a marker on a tool handle can identify which laparoscopic tool is used. The geometry of the tool is then known, as well as the distance from the marker to the tip of this instrument. The distance from the marker to the "smart" trocar camera can be computed from a video camera on the trocar, and combining both distances, the position of the tip of the instrument in the trocar coordinate system can be obtained.

In certain embodiments, computation of the position of the trocar position in the operating room coordinates is obtained by recognizing a reference marker on the wall or ceiling of the operating room.

Certain embodiments may comprise individual components, including for example: (1) a trocar with a wireless camera; (2) markers on the handle of the tool as well as the wall or ceiling of the operating room; and (3) a computer system that processes the video generated by the smart trocar in real time.

Another aspect of the present disclosure is directed to a method of tracking a surgical tool. The method may include providing a surgical tool to a surgical port where the surgical tool may include a tracking element and the surgical port may include a camera mounted thereto. The method may further include capturing image data at the camera. The method may further include providing the image data to a processor and determining, at the processor, tracking information associated with the surgical tool.

A further aspect of the present disclosure is directed to an information management system for managing medical procedure information. The system may receive image data from a camera associated with a surgical port, the image data representative of a reference marker and/or a tracking element associated with a surgical tool. The image data is not associated with a particular finite set of known tools. The system may further determine an identity and a location of the surgical tool based on the image data. The system may also determine a surgical step of a medical procedure using the image data and determine procedure management information by comparing the image data associated with the surgical step with the medical procedure.

The details of one or more embodiments of the invention are set forth in the accompanying drawings and the description below.

Certain terminology is used in the following description are for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "approximately" or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments of the present disclosure are provided in the following drawings. The drawings are merely examples to illustrate the structure of exemplary devices and certain features that may be used singularly or in combination with other features. The invention should not be limited to the examples shown.

FIG. 21 is a table showing results of an experiment on two translations (in cm) and two rotations (in degrees) according to exemplary embodiments.

DETAILED DESCRIPTION

Figure 1:
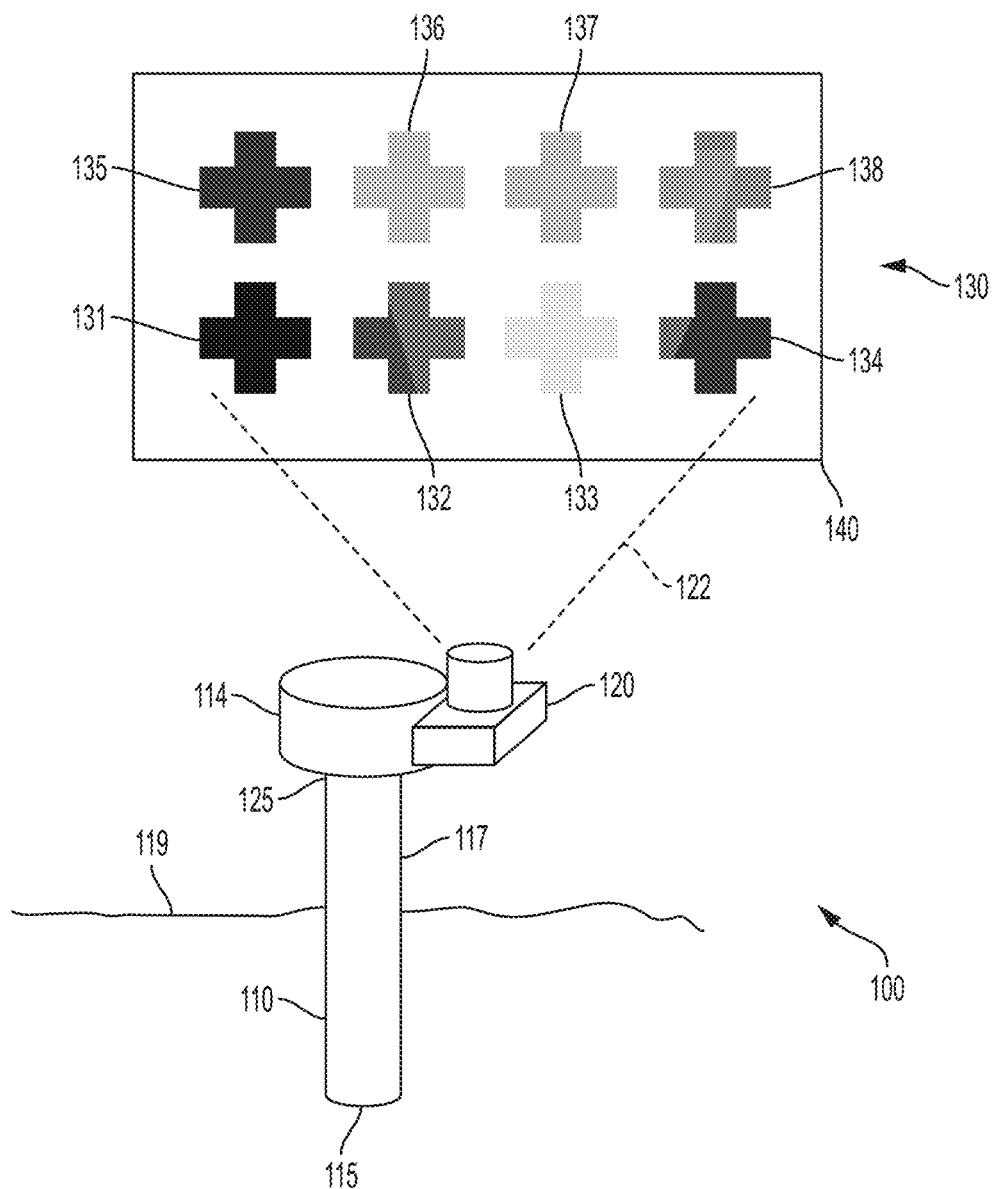
FIG. 1 is a schematic view of an example system configured for surgical tool global positioning.
Figure 2:
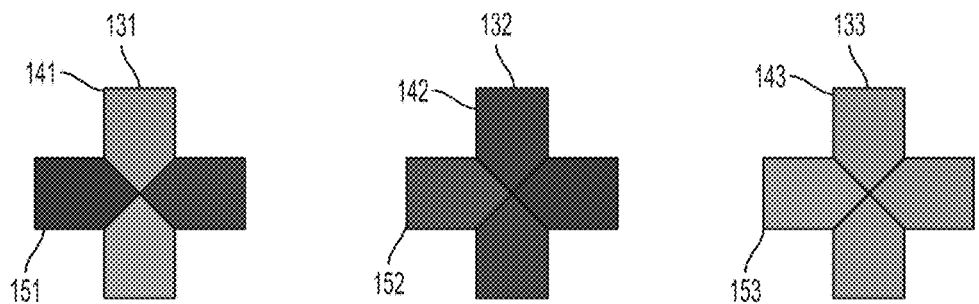
FIG. 2 is view of example reference markers of the system of FIG. 1.

Referring now to FIGS. 1-2, a system 100 configured for surgical tool global positioning is displayed. In the embodiment shown, system 100 comprises a surgical port 110 comprising a proximal end 125 configured to be located outside a body of a patient 119 and a distal end 115 configured to be located within an internal portion of the body of patient 119. In the illustrated embodiment, surgical port 110 comprises a channel 117 extending between proximal end 125 and distal end 115.

In the embodiment of FIGS. 1-2, system 100 further comprises a plurality of reference markers 130 positioned at a first fixed location 140 distal to surgical port 110. In the embodiment shown, the plurality of reference markers 130 comprises individual reference markers 131-138. In particular embodiments, fixed location 140 may be positioned on the ceiling of a room in which surgical port 110 is located, including for example, a ceiling of an operating room.

In addition, the embodiment of system 100 shown comprises a camera 120 coupled to proximal end 125 of surgical port 110. In this embodiment, camera 120 comprises a field of view 122 configured to capture image data associated with one or more reference markers 131-138. As shown in FIG. 2, reference marker 131 may comprise a first segment 141 intersecting with a second segment 151 to form a cross shape. Similarly, reference marker 132 comprises intersecting segments 142 and 152, while reference marker 133 comprises intersecting segments 143 and 153. The remaining reference markers 134-138 can be similarly constructed. It is understood that the geometry, arrangement and number of reference markers shown is merely one example of several different configurations possible in embodiments of the present disclosure.

As explained in more detail below, image data associated with one or more reference markers 131-138 may be used to determine a global position of surgical port 110, as well as a tool inserted into surgical port 110.

Figure 3:
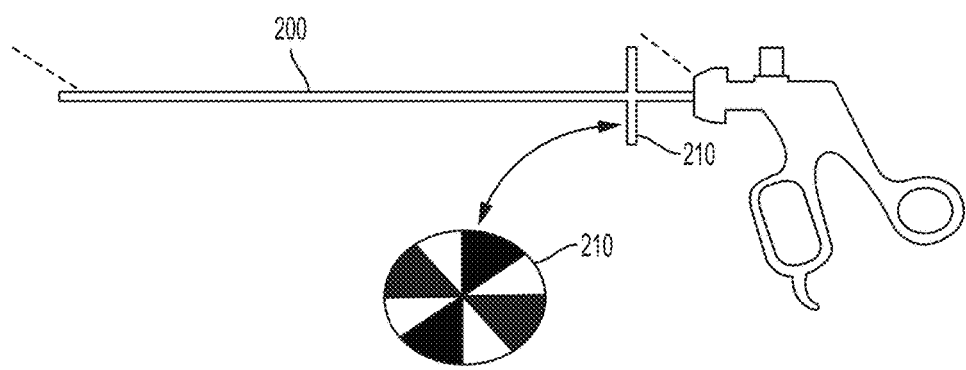
FIG. 3 is a schematic diagram of an example tool configured for use with the system of FIG. 1.

Referring now to FIG. 3, a tool 200 is configured for insertion into surgical port 110 (shown in FIG. 1). In this embodiment, a tracking element 210 is coupled to surgical tool 200. As shown in FIG. 3, tracking element 210 is circular in shape and includes a pattern of geometric shapes on one side (e.g. segments of a circle in this embodiment). During use, tool 200 may be inserted into surgical port 110 such that the circular shape and pattern of tracking element 210 can be detected by camera 120. In certain embodiments, tracking element 210 may be configured similar or equivalent to the tool identification marker as disclosed in U.S. patent Ser. No. 14/099,430, incorporated by reference herein. Particular embodiments may also comprise separate cameras for detecting image data associated with tracking element 210 and reference markers 131-138.

In exemplary embodiments, surgical port 110 can be placed into an incision in the body of patient 119 and provide an access point through which surgical instruments may be introduced into an internal surgical site. In certain embodiments, surgical port 110 can include a needle, a cannula, a trocar, or any other style of surgical port known in the art. Surgical port 110 can be composed of a biocompatible material. It is contemplated that the surgical port 110 can be constructed from a disposable material thereby reducing cost and avoiding problems of sterilization and battery change. Surgical port 110 can have a proximal end 125 configured for location on the outside of the patient's body and a distal end 115 sized and configured to extend into the internal portion of the patient's body. Channel 117 can extend through surgical port 110 to provide access to an internal portion of the patient's body such that a surgical tool 200 (e.g. a laparoscope, endoscope or other tool as shown in FIG. 3), can be inserted into the patient's body via channel 117.

Exemplary embodiments of surgical tool tracking system 100 can include a camera 120 mounted to proximal end 125 of surgical port 110. Camera 120 can capture visible spectrum and/or infra-red light or include any other imaging modality suitable for use with surgical procedures. Camera 120 can be configured to capture and store video and/or still images. Camera 120 may also be configured to capture and store audio data. Camera 120 can be configured to capture image data associated with reference markers 130 and tracking element 210 including still and/or video images. Camera 120 may be further configured to capture image data associated with a surgeon performing the medical procedure. For example, camera 120 can capture image data providing surgeon-identifying information such as a surgeon-specific tracking element or marker. An example surgeon-specific marker can include a particular colored glove worn during the medical procedure. The image data associated with the surgeon can also include motion information with respect to surgical tool 106 and/or the surgeon's hand. The motion information can be used to track the motion/path of the surgeon's hands and/or surgical tool 106 during the medical procedure.

In certain exemplary embodiments, camera 120 can be coupled to surgical port 110 via mounting to base 114 of proximal end 125. In other exemplary embodiments, camera 120 can be incorporated with or otherwise integral to base 114. The location of camera 120 with respect to the surgical port 110 can be fixed such that camera 120 can be mounted to or otherwise incorporated into the base 114 at a fixed and set position. In other embodiments, the location of camera 120 can be changed or adjusted with respect to surgical port 110. For example, camera 120 can be mounted to base 114 using an adaptor that controls the position and orientation of camera 120.

In certain embodiments, camera 120 can be mounted to the base 114 such that the optical lens/field of view of camera 120 is directed away from the body of the patient. For example, camera 120 can be mounted to the base 114 such that the optical lens/field of view of camera 120 is provided in a direction of reference markers 131-138, tracking element 210 and/or the surgeon's hand as surgical tool 200 approaches and/or is inserted into surgical port 110. In a further example, camera 120 can be mounted to base 114 such that the optical lens/field of view of camera 120 is both directed away from the body of the patient and in a direction of reference markers 131-138, tracking element 210 and/or the surgeon's hand as surgical tool 200 approaches and/or is inserted into surgical port 110. For example, it is contemplated that the optical lens/field of view of camera 120 can be configured to capture image data of reference markers 131-138, tracking element 210 and/or surgeon's hand as surgical tool 106 approaches and is located within surgical port 110.

In particular embodiments, camera 120 can include a light element for illuminating reference markers 131-138, tracking element 210 and/or the surgeon. For example, light element can include an ultraviolet LED that illuminates a UV sensitive feature on reference markers 131-138 and/or tracking element 210. The use of a non-visible light range should not disturb a surgeon preferring to operate in low light conditions. Use of the a UV sensitive feature on reference markers 131-138 and/or tracking element 210 can also have positive effects on the recognition process because reference markers 131-138 and tracking element 210 will appear to the system a bright and colorful item in the image, thus making it more distinguishable from the background and/or image noise.

In certain embodiments, camera 120 may be capable of operating on a wired or wireless communication network. Camera 120 may be configured to communicate with other devices using the communication network, the other devices including computers, personal data assistants (PDAs), mobile telephones, and mobile computers. For example, tracking system 100 can include a computer system (not shown). Camera 120 can be in communication with the computer system to transmit image data to the computer system for analysis and/or storage. Tracking system 100 may include other components capable of acquiring, storing, and/or processing any form or type of data. Any such component may be coupled to or integrated into base 114 or may be communicatively coupled to tracking system 100 and/or the computer system.

As explained in further detail below, image data obtained by camera 120 and associated with reference markers 131-138 can be used to calculate a global position of laparoscopic tool 200. In the mathematical equations presented herein, it is assumed that the geometry and shape of laparoscopic tool 200 with precise measurement is known. In principle, this information can be provided by the vendor for tool 200. It is also assumed tracking element 210 has a rigid attachment to the tool and is perpendicular to the axis of the tool. The location of the tracking element 210 on the axis is known as shown in FIG. 3.

The motion of laparoscopic tool 200 is channeled by surgical port 110. The motion can be decomposed into: (a) a translation along the main axis of surgical port 110; and (b) a small deviation from the port axis allowed by the difference in diameters between surgical port 110 and tool 200.

The position of the tool 200 in a coordinate system coupled to surgical port 110 can then be determined. If the axis of tool 200 is perfectly aligned to the axis of surgical port 110, the distance from tracking element 210 to surgical port 110 can be computed from the apparent diameter of tracking element 210 in the image data (e.g. video stream). If the port and tool axes are not aligned, tracking element 210 will appear as an ellipse, instead of a circle, in the image data. The axis of the ellipse small diameter and the axis of laparoscopic tool 210 can provide the plan of the rotation.

Figure 4:
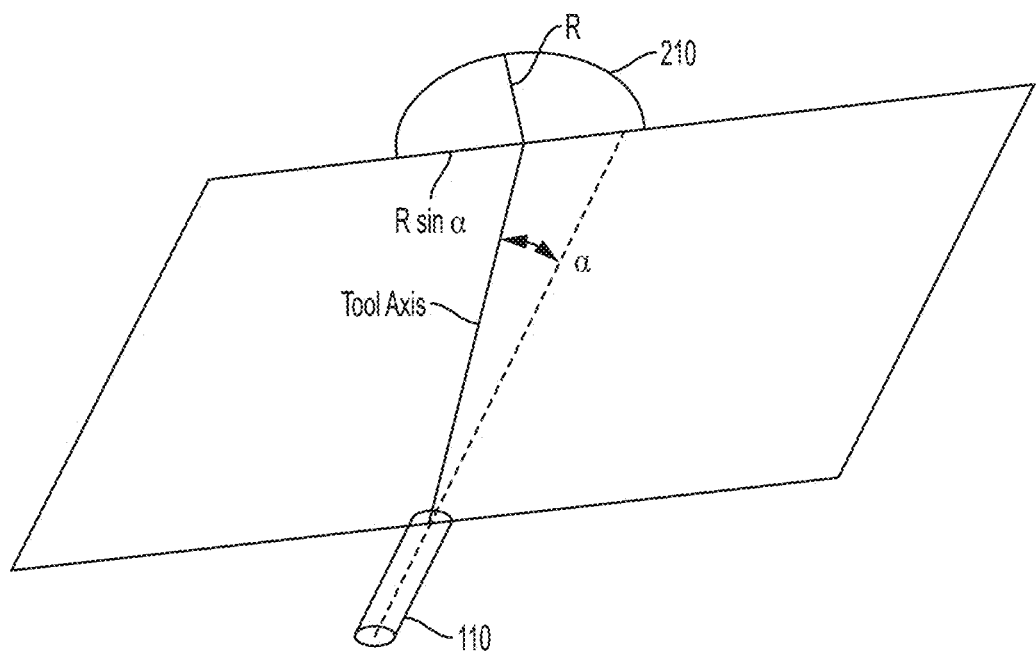
FIG. 4 is a schematic view of a tracking element configured for use with the tool of FIG. 3.

The ratio of the largest diameter of the ellipse to the smallest diameter of the ellipse can provide the angle $\alpha$ via a basic trigonometric formula (see FIG. 4). In practice, a will be small because the diameter of tool 200 is close to that of surgical port 110. For example, a port that is 5 inches in length with a diameter 2 mm larger than the inserted tool will result in a maximum angle $\alpha$ of approximately 1 degree. Based on the geometric constraints and formulas described above, it is possible to localize an end of tool 200 in a coordinate system coupled to surgical port 110.

Figure 5:
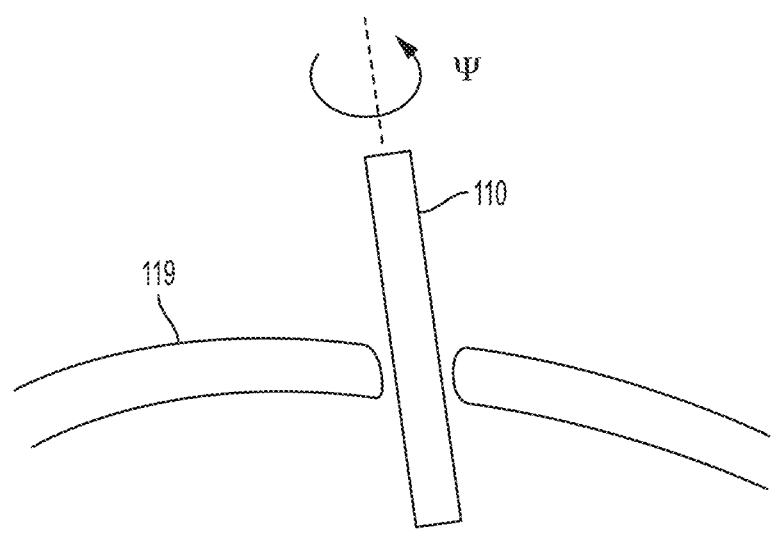
FIG. 5 is a schematic diagram of a surgical port of the system of FIG. 1.
Figure 6:
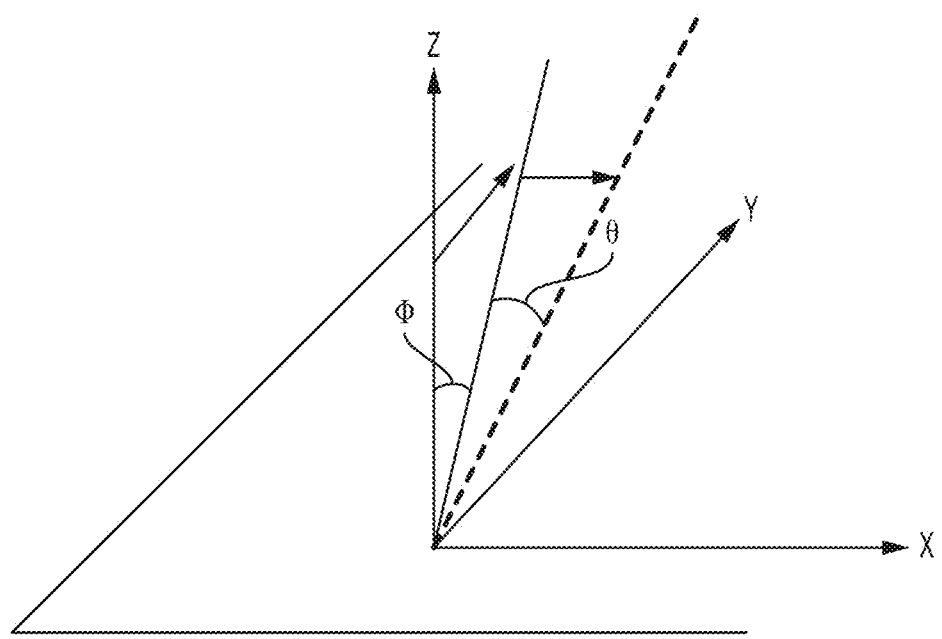
FIG. 6 is a schematic of the surgical port of the system of FIG. 1 in a coordinate system.

Surgical port 110 can have complex motion in three dimensions. Referring now to FIG. 5, the body of a patient 119 has elasticity, and port 110 can change angle in two independent spatial directions. The motility of patient 119 (e.g. an abdominal wall) can be used by the surgeon to direct the end of tool 200 in the region of interest (ROI). The orientation of the axis of port 110 in the (x, y, z) coordinate system of the operating room corresponds to two unknown angles denoted $\theta$ and $\Phi$ in FIG. 6. In addition, patient 119 or the support surface (e.g. operating room table) can move during the procedure due to breathing or other movements. Larger movements may correspond to the fact that the surgeon modified the angle of inclination of the support surface to facilitate access to the region of interest. The displacement of location at which port 110 enters patient 119 in three spatial directions is denoted by dx, dy, and dz.

Figure 7:
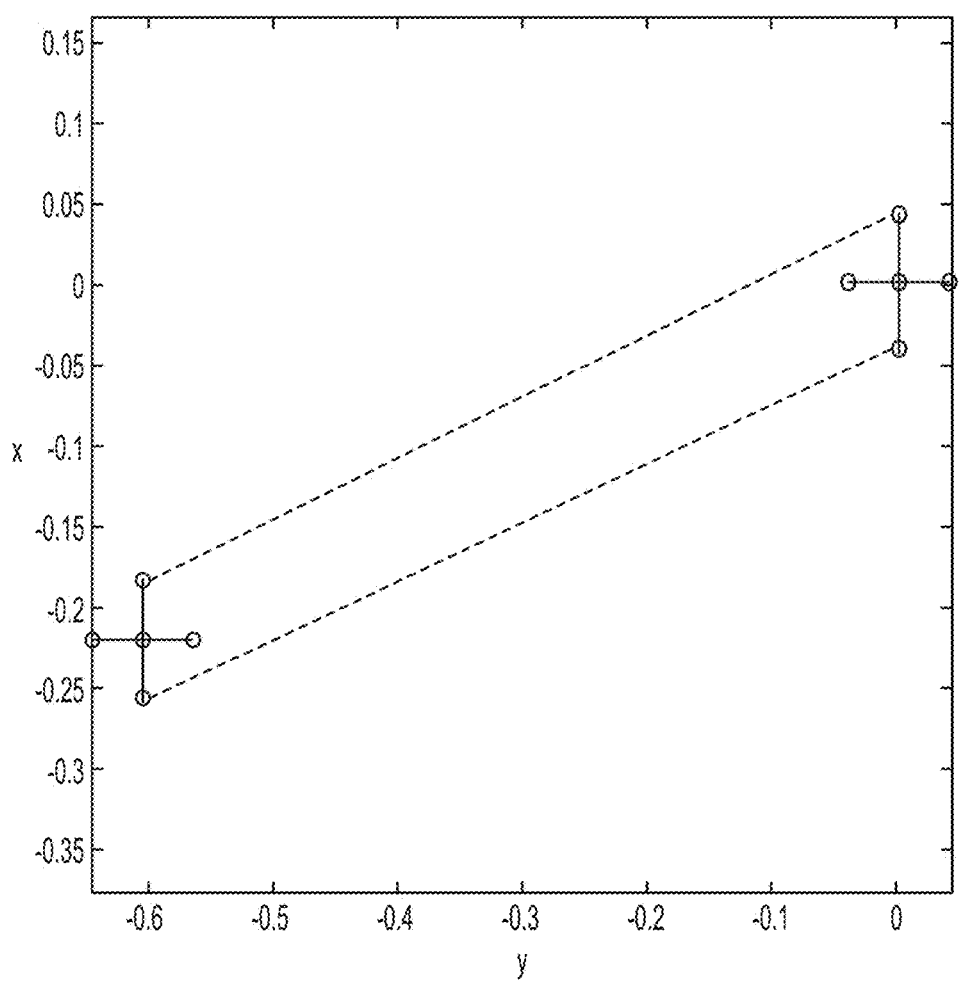
FIG. 7 is a graph of the trajectory of a reference marker of the system of FIG. 1.

Referring now to FIG. 7, image data (e.g. captured by camera 120) associated with a cross-shaped reference marker (e.g. one of reference markers 131-138) is displayed. From this image data, one can extract the trajectory of five points corresponding to the end points of the intersecting segments and the center of the reference marker. This trajectory corresponds to the motion of surgical port 110. As shown in the sections below entitled "A1 Method" and "A2 Experiment", mathematical calculations can be performed to determine $\theta$, $\Phi$, dx, dy, and dz. With these values known, one can then reconstruct the spatial trajectory of surgical port 110 in a coordinate system established, for example, in an operating room.

Combining the above parameters and calculations can provide a complete three-dimensional, real-time positioning system for a rigid laparoscopic tool and the tip or end of the tool.

In general, if the tool has mobile parts such as a scissor insert as shown in FIG. 3, one will need to identify the motion of the mobile parts versus the main body of the tool. In many cases, this can be done with a single degree of freedom. One can reconstruct the angle of the opening of the scissor from the image data (e.g. video streaming from an endoscope) to fully reconstruct the position of the tool. Simulated results indicate that accuracy can be obtained on the order of one millimeter for the position of a tool inside an abdominal cavity, and preliminary experimental results confirm the theoretical result.

In certain embodiments, the view angle of camera 120 may be limited and/or obstructed. It may therefore be desirable to include a plurality of reference markers on the ceiling of the operating room. Such a configuration can help to ensure that the system has sufficient input data and can ensure accuracy since the system can use redundant computation. In certain embodiments, the least square fitting method can be used to limit the impact of errors in the pattern recognition of the reference markers. This redundancy may also be used to correct optical distortion when the reference markers are far from the optical axis of the camera. Similarly, in the unlikely event that the surgical port rotates in the plan perpendicular to its axis, one can retrieve the angle of rotation ($\psi$) as shown in FIG. 5, since there will be multiple reference marker shapes (e.g. crosses of intersecting segments) to reconstruct the additional unknown.

It has been observed that an approximation of the position of a patient abdominal wall can be obtained by virtue of the smart trocars attached to the wall. Provided that one has a three-dimensional reconstruction of the anatomy of the patent in the operating room, one can position the tip of the laparoscopic tool with respect to anatomical structures. The operating room system should then be able to provide information to the surgeon on locations that should not be crossed by the crossed by the laparoscopic tool (e.g. a "secure no fly zone" used in training, but not currently in actual clinical conditions). Similarly, if an optimum access position has been decided during preparation of the operation, the system can guide the surgeon to that optimum maneuver.

Embodiments disclosed herein provide a low cost system that does not require new techniques from the surgeon. In addition, the system is robust and accurate, can be installed in a standard operating environment. The system also does not present additional risks to patients.

It is understood that the methods and mathematical models described in the sections below are exemplary of one embodiment, and that other embodiments are contemplated in this disclosure. For example, while a trocar is referenced in the discussion below, other types of surgical ports may be used in other embodiments.

A1 Method

For clarity, most of the mathematical presentation below is restricted first to motion in the vertical plan (x,z) that contain trocar. We will discuss briefly second the generalization to three spacial dimension in the (x,y,z) coordinate system of the OR.

Rotation:

Let us consider a rotation of the trocar clockwise in the (x,z) plan. We note this rotation $\tau_\theta$. The trocar has a fixed point that is the center of the rotation. Let us assume that the trocar and the marker denoted by the triplet ($x_{-1}, x_0, x_1$)) are in the same vertical plan.

We consider first the direct problem: given $\theta$, what would be the position of the marker in the new image?

Figure 8:
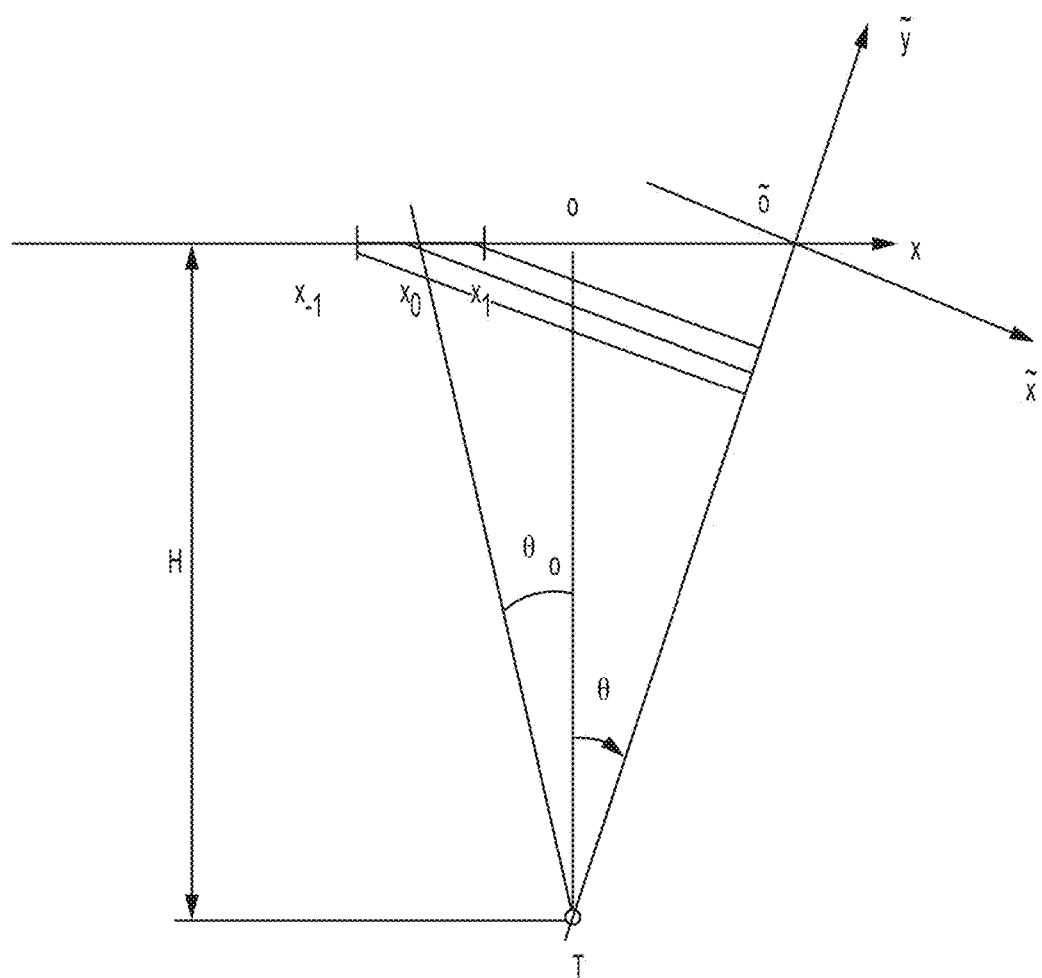
FIG. 8 is a schematic of the rotation of the surgical port of the system of FIG. 1.

In the new coordinate system ($\tilde{x}$, $\tilde{y}$)—see FIG. 8—the coordinate of the marker ($\tilde{x}_{-1}, \tilde{x}_0, \tilde{x}_1$)), is, for j=-1, 0, 1:

$$\tilde{x}_j = \cos(\theta)(-H\tan(\theta) + x_j), \quad (1)$$

$$\tilde{y}_j = \sin(\theta)(-H\tan(\theta) + x_j), \quad (2)$$

Figure 9:
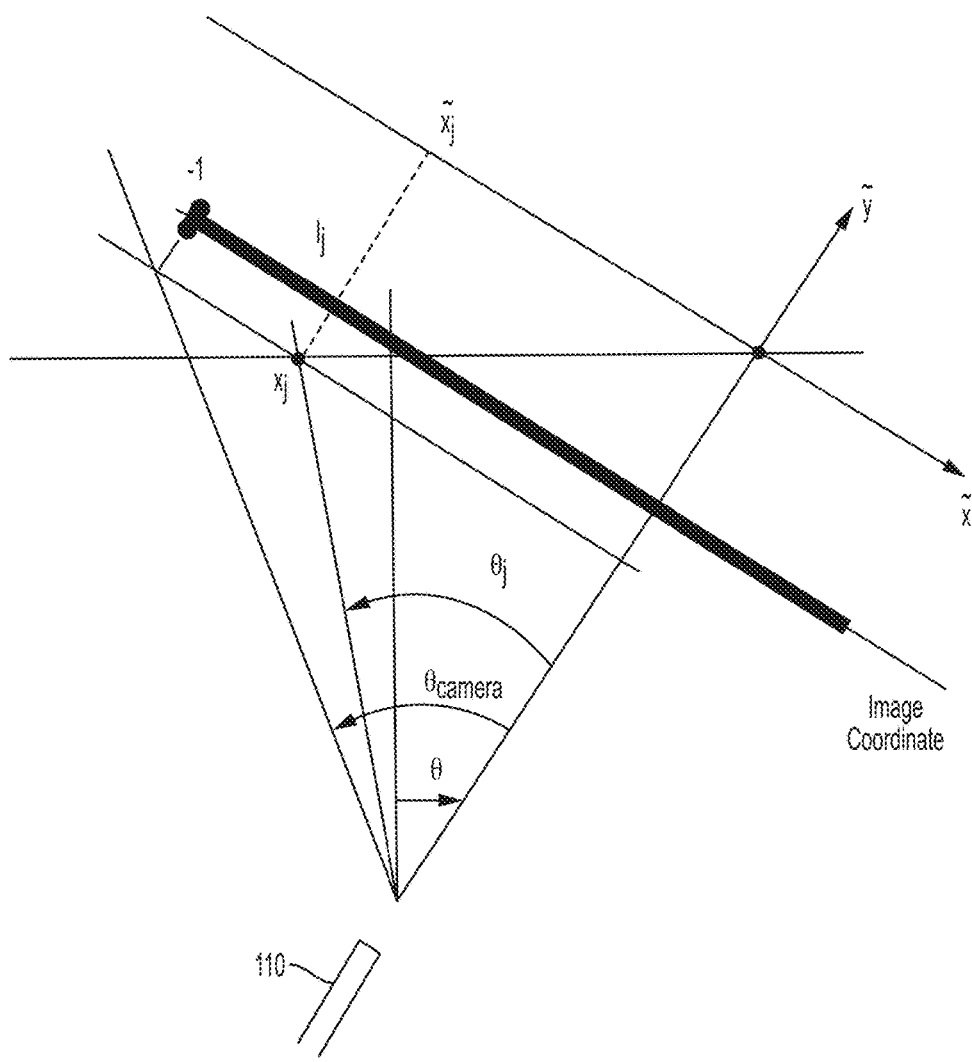
FIG. 9 is a schematic of the relationship of the surgical port of the system of FIG. 1 to new image coordinates.

Let us denote $\Theta_c$ the view angle of the camera—see FIG. 9—The physical dimension of the new image frame is ($-\tilde{L}$, $\tilde{L}$), on the line is $\tilde{y} = \tilde{y}_j$, is:

$$\tilde{L} = \tan\left(\frac{\Theta_c}{2}\right)\left(\frac{H}{\cos(\theta)} + \tilde{y}_j\right). \quad (3)$$

The position of the marker $x_j$ in the image (−1,1) will be $$\tilde{I}_j = \frac{\tilde{x}_j}{\tilde{L}}. \quad (4)$$

For any landmark of coordinate $x_j$ in the initial image, the map $$\theta \to \tilde{I}(x_j)$$

for the range of rotation we do consider is bijective. As a matter of fact this map is a strictly decreasing function of $\theta$. The inverse problem consist to solve the non linear set of equation (1) to (4) with for example a Newton scheme.

Figure 10:
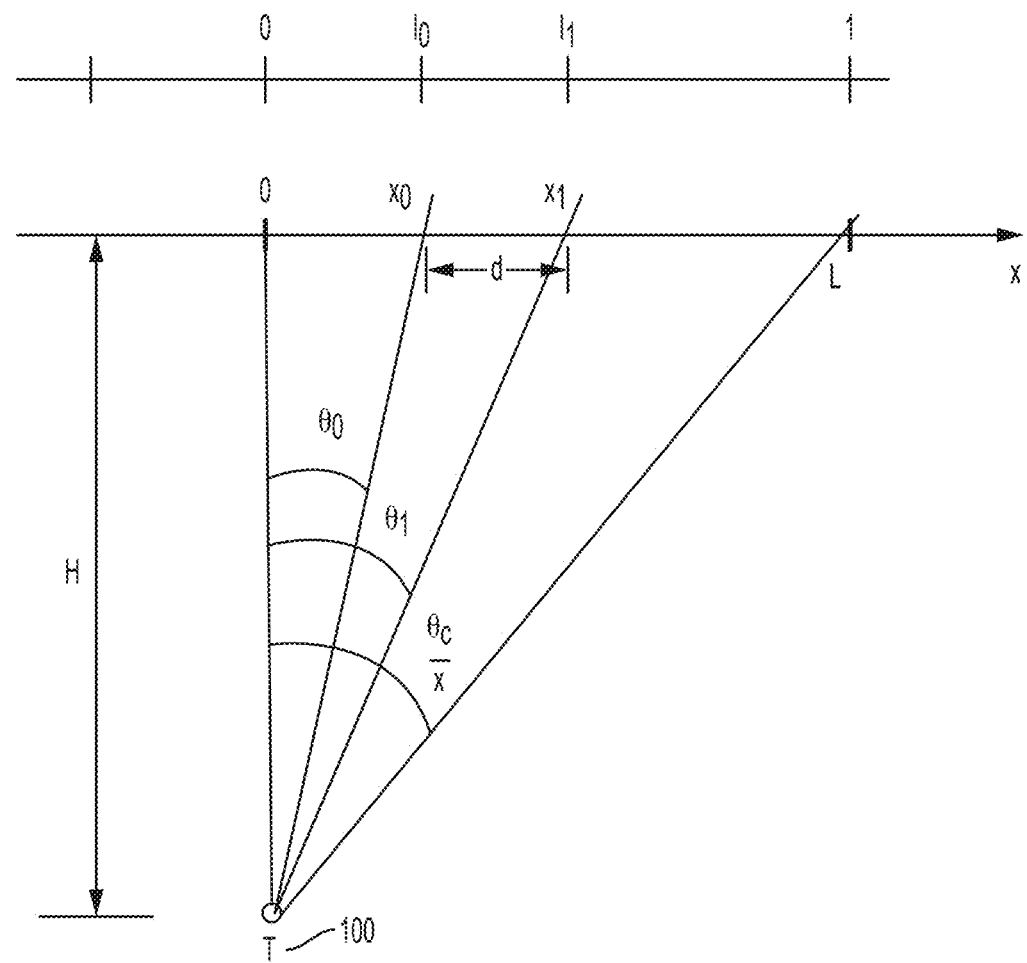
FIG. 10 is a schematic of the initial reconstruction of the coordinates of the surgical port of FIG. 1.

However we have assumed that the initial position of the trocar in the OR was given. Let us show that this problem can be solved with two landmarks—See FIG. 10. The two unknown are the physical location of point O at the vertical of the trocar and the distance between the trocar and the ceiling denoted H. For simplicity we will still restrict ourselves to the (x,z) plan. The generalization to 3d is straightforward.

To start we get the coordinate $I_0$ and $I_1$ of the landmark $x_0$ and $x_1$ in the image. We know also a priori the physical dimension d=$x_1$−$x_0$, of our marker.

We have:

$$\tan(\theta_0) = \frac{x_0}{H}, \tan(\theta_1) = \frac{x_1}{H}, \tan\left(\frac{\theta_c}{2}\right) = \frac{L}{H}. \quad (5)$$

and $$x_0 = I_0 L, x_1 = I_1 L. \quad (6)$$

We obtain:

$$H = d\left((I_1 - I_0)\tan\left(\frac{\theta_c}{2}\right)\right)^{-1}.$$

and $$x_0 = I_0 H \tan\left(\frac{\theta_c}{2}\right), x_1 = I_1 H \tan\left(\frac{\theta_c}{2}\right).$$

This conclude the reconstruction of the rotation of the trocar by tracking the landmarks on the ceiling.

However the motion of the trocar can be more complex and involve two translations in respectively x and z direction. We will denote dx and dz this displacement and as before $\theta$ the rotation.

Translation:

To take into account these two translations, denoted $\tau_{dx}$ and $\tau_{dz}$, the landmark of initial coordinate $x_j$ has for new coordinates $$\tilde{x}_j = \cos(\theta)(-H - dz \tan(\theta) + x_0 - dx), \quad (7)$$

$$\tilde{y}_j = \sin(\theta)(-H - dz \tan(\theta) + x_0 - dx), \quad (8)$$

We have now three unknowns that are dx and dy and $\theta$. We need then three landmarks. We needs to solve the nonlinear set of equations with the image coordinate $I_{-1}$, $I_0$, $I_1$ from three landmarks. We can use a Newton scheme to solve numerically that non linear problem, since we can explicitly compute the Jacobian of the system. So far we have restricted ourselves to two space dimension and we worked with a combination of three geometric transform:

$$\tau_\theta o \tau_{dx} o \tau_{dz}.$$

A similar reasoning can be applied in three apace dimensions. We consider the three d coordinate system (x, y, z) of the OR. We work with the transformation:

$$\tau_\theta o \tau_\phi o \tau_{dx} o \tau_{dy} o \tau_{dz}.$$

We need then to identify 5 unknowns $\theta$, $\phi$, dx, dy, dz and will need 5 landmarks. We wrote with a matlab code a small simulator based on a cross motif—see FIG. 7. This code applies successively each transformation to the image viewed from the trocar. This simulator help us to compute the sensitivity of the system. Let us assume that the image comes with a resolution of 500 pixels in each dimension. One can show from simulation that an accumulated error of 4 pixel in each spatial direction will result in an error of about 1 mm at the end of the laparoscopic tool. This error is very small indeed because the relative distance from the trocar to the ceiling is much larger than from the trocar to the ROI inside the abdomina cavity.

The exact accuracy of the system needs to be checked with an experiment that will carry various type of uncertainties, from optical defect of the camera, imperfection in focussing, and noise in the image segmentation of the landmark. We expect however to have a fairly robust and accurate result from our design. Next we will present some preliminary experimental results that validate our approach.

A2 Experiment

Our goal here is to validate the quality of the method to reconstruct separately each component of the motion of the trocar, from tracking the landmark on the ceiling.

Figure 11:
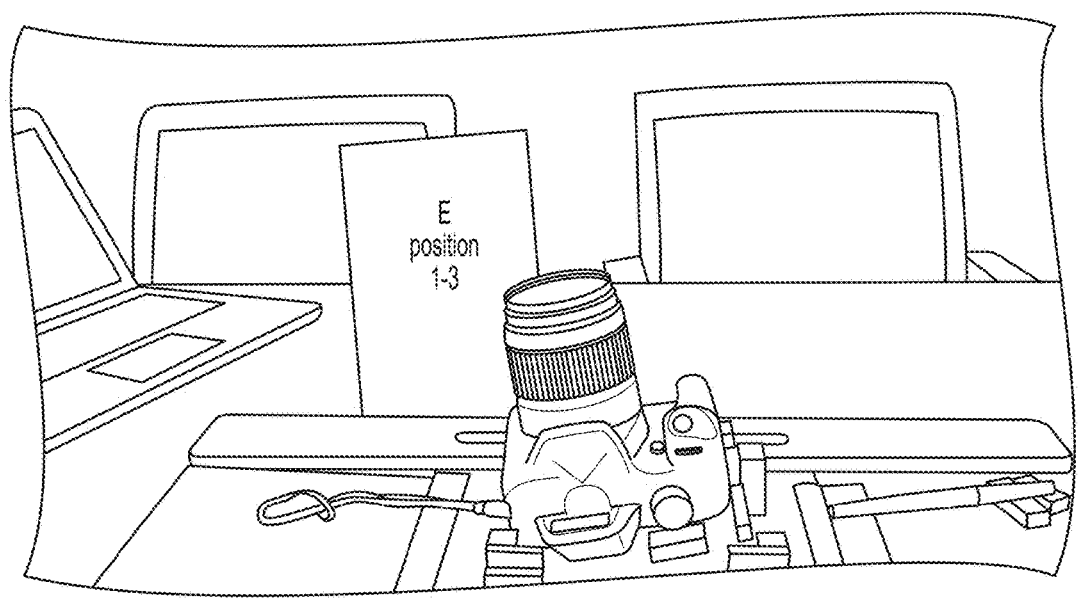
FIG. 11 is a photograph of the camera used to validate data acquired by the system of FIG. 1.
Figure 12:
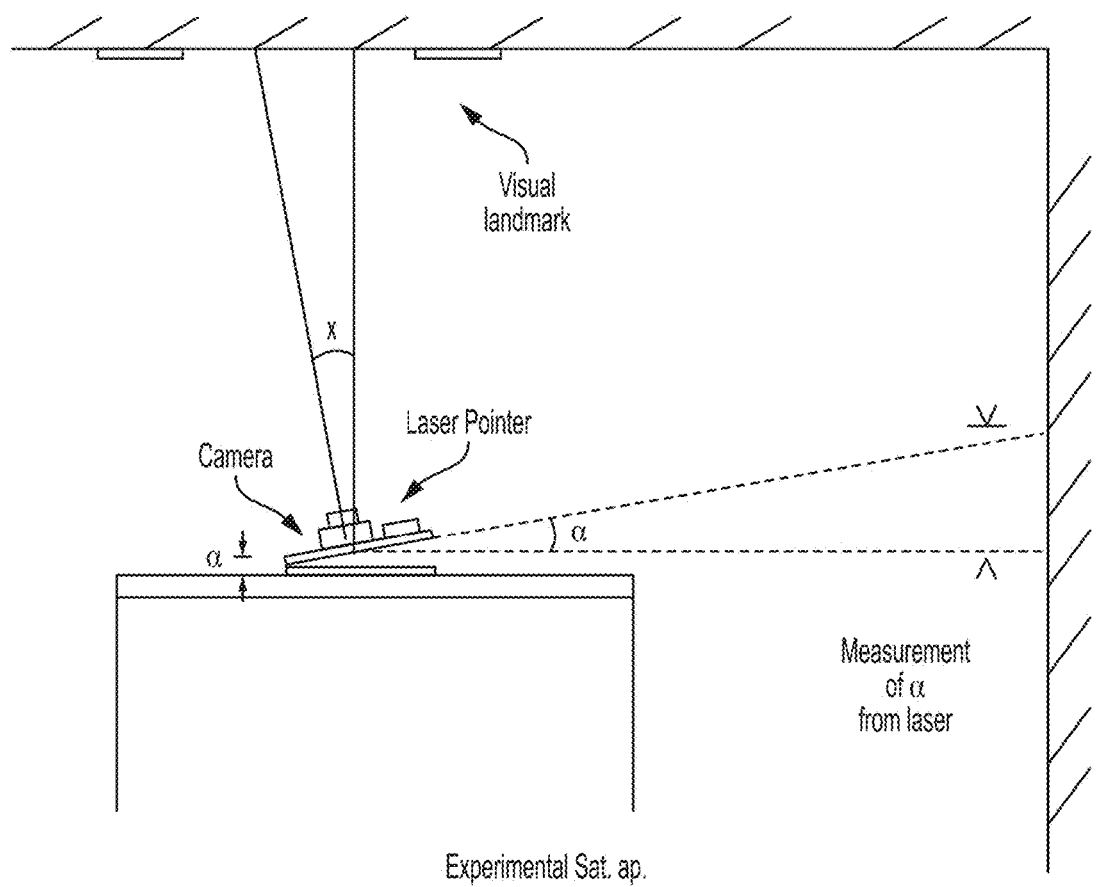
FIG. 12 is a schematic of the camera of FIG. 11.

Rotation:

Let's start with the rotation component in one space direction. FIGS. 11 and 12 show a rapid prototyping to check that result.

Figure 13:
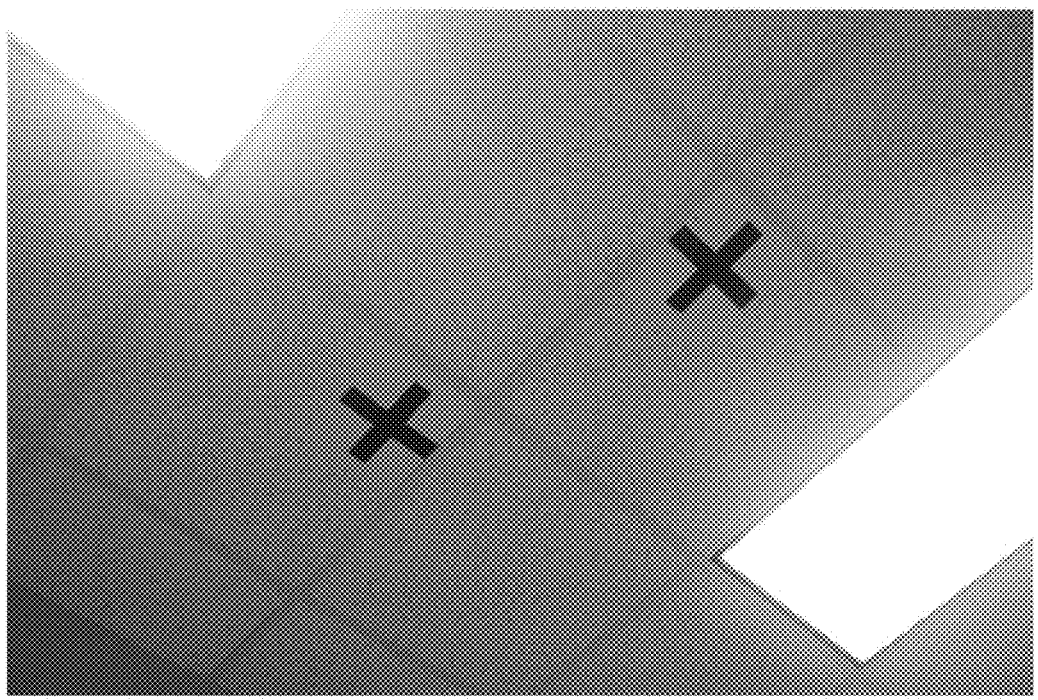
FIG. 13 is a photograph of reference marks.
Figure 14:
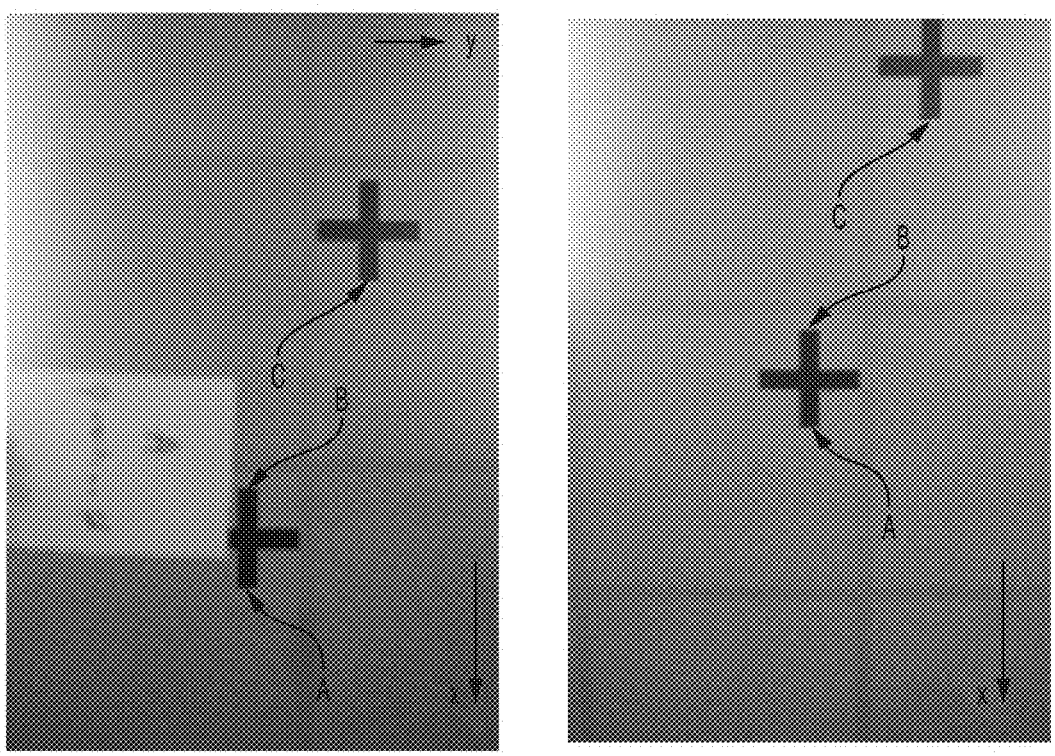
FIG. 14 is a photograph of reference marks before and after rotation.

We have set on the ceiling two black crosses that are visible from the digital camera—see FIG. 13. We set first the camera in the flat position, and measure on the wall the height of the laser beam projection. We shoot in that position an image of the ceiling—see FIG. 14 on left. The auto focus option of the camera was turned off. The image of the ceiling is somehow out of focus. We made this image noisy on purpose to get more realistic conditions.

We set second the camera in a position that forms a small angle with the desk as in FIG. 11. We measure on the wall the new position of the laser beam projection. From these two measures on the wall, we get the angle $\alpha$ with an accuracy of about 0.5° We shoot in that new position an image of the ceiling see FIG. 14 on right.

We observe indeed the displacement of the markers due to the change of orientation of the camera.

We apply then our algorithm to reconstruct the angle $\alpha$ from these two images: first we compute the coordinate of the three points A, B and C using the graphic interface of the GIMP2 software. An automatic image segmentation will be actually more accurate.

Figure 15:
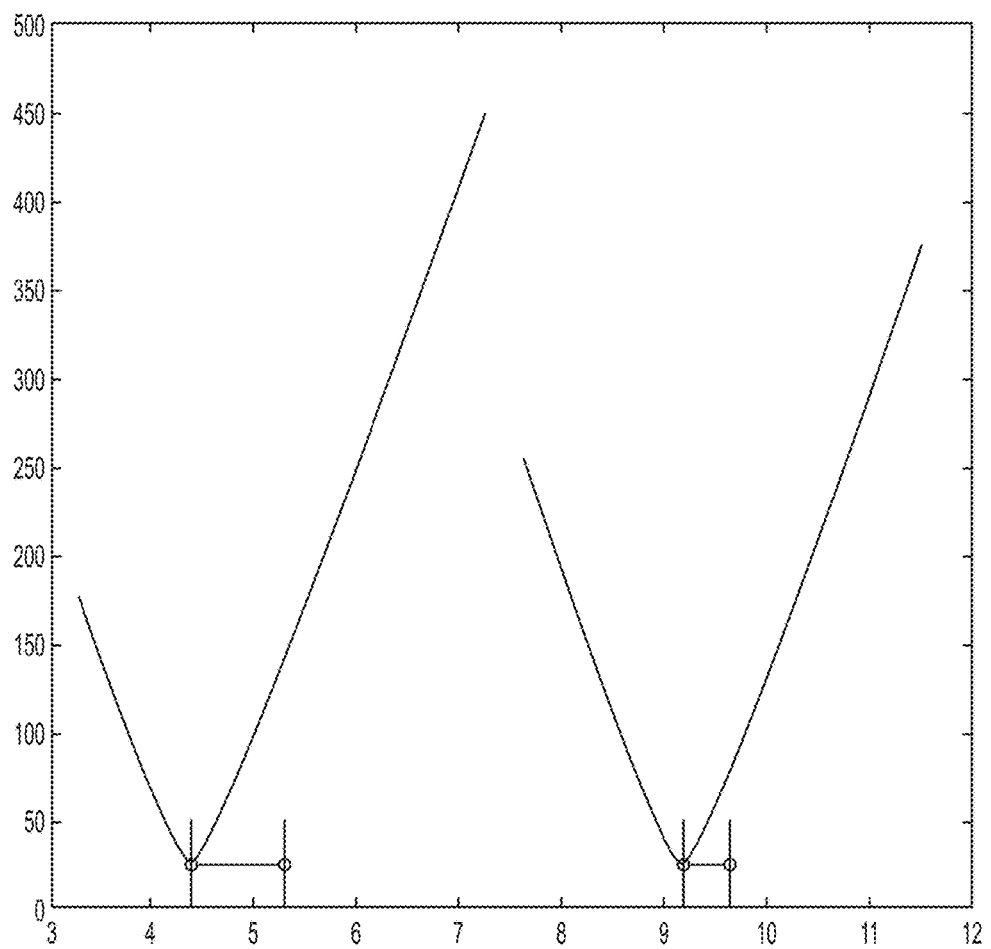
FIG. 15 is a graph of a computational result with different angles.

Second we map the transform we defined earlier $$\theta \rightarrow \tilde{I}(x_j)$$

and look for the angle that minimize the matching between the computed coordinate of the point A, B and C after rotation, in the L2 norm—FIG. 15. Our result are for $\alpha=5.3°$ and $\alpha=9.6°$. Our algorithm based on computer vision gives: $\alpha=4.4°$ and $\alpha=9.2°$. We did this experiment several time, and observe a good reliability of the method.

In other words we get an error of less than a degree on the trocar position. This may represent an error on the lateral position of the tip of a laparoscopic tool of the order of 3 mm for a ROI with a 20 cm depth from the abdominal wall.

Translation:

Next let us consider a different displacement of the trocar that can be for example resulting from the patient breathing.

We have run a similar experiment to check the accuracy of a displacement of the "trocar" in the vertical direction z toward the ceiling. Here the camera stays flat, and we change the thickness of the support, to increase the height of few centimeters. Lets denote $\delta z$ the increase in thickness of the support. For $\delta z=2$ cm we get from our computer vision algorithm a computed value of $\delta z=1.62$ cm. Similarly for $\delta z=3$ cm we get from our computer vision algorithm a computed value of $\delta z=3.23$ cm. Overall the error on the vertical displacement is less than 4 mm. We suspect that we can improve much that result by using landmarks separated by larger distances.

The idea of fixing patterns on the ceiling is due to the need to locate precisely the surgical system. In a first approach and to facilitate the detection we added identifiable markers to give our GPS data to compare between two frames. Let us assume that we have painted a cross on the ceiling, and that this cross is captured by the video stream from the wireless camera. We can extract from the video the trajectory of four points that can be the end point of the cross. This trajectory corresponds to the motion of the trocar. It is important that we can see a cross for every position, one cross is not sufficient this imply to use colored patterns that we know the characteristics: position of cross and color. Now that we know how our localization system looks like we can model it with equations. In order to get the proper localization information we have to solve a specific system based on geometry. The scheme below in FIG. 16 shows the coordinate system that we use in the rest of this document.

Figure 16:
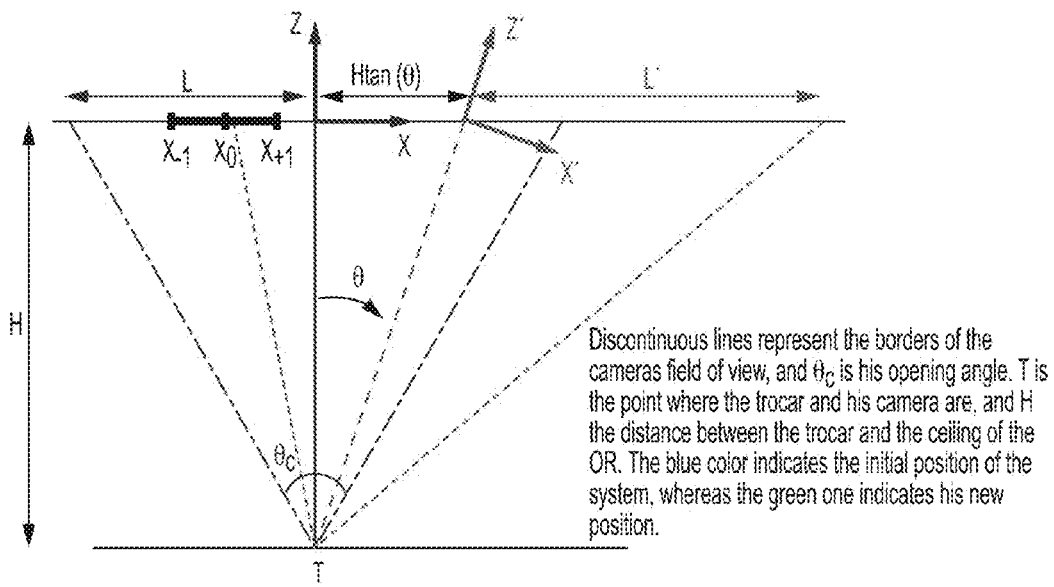
FIG. 16 is a geometrical schematic of exemplary embodiments.

As we can see, $X_{-1}$, $X_0$ and $X_{+1}$ are feature points of the markers on the ceiling and those feature points are used to express in the coordinates system after a motion described by a translation dZ on the Z axis, a translation dX on the X axis and a rotation $\theta$ around the Y axis (as shown in FIG. 16). For clarity, most of the mathematical presentation below is restricted first to motion in the vertical plane (x,z) that contain the trocar. We will discuss the generalization to three spacial dimension in the (x,y,z) coordinate system of the OR. In this initial state, the system can be represented by the following equations:

$LX=\tan(\theta_C/2)H$, real portion of the ceiling viewed by the camera on the $X$ axis $xL_X=colX$, proportionality between image ($x$ and col) and reality ($X$ and $L_X$)

where x is the image coordinate, X the real coordinate and col the number of columns.

The motion of the trocar can be complex. Let us consider a rotation of the trocar clockwise in the (x,y) plan and two translations. We note /theta the rotation, dX and dZ the translations. The trocar has a fixed point that is the center of the rotation. Let us assume that the trocar and the marker denoted by the triplet $(X_{-1}, X_0, X_{+1})$ are in the same vertical plan. Now we can express the new image coordinate x' for the new real position X' of the trocar. The system of equations below enables us to achieve this goal. So, on the X axis we have:

$X'=\cos(\theta)(-(H+dZ)\tan(\theta)+X+dX)$, new real $X$ coordinate $Z_{X'}=\sin(\theta)(-(H+dZ)\tan(\theta)+X+dX)$, new real $Z$ coordinate $L_{X'}=\tan(\theta_C/2)(H/\cos(\theta)+Z_{X'})$, new part of the ceiling viewed by the camera $x'L_{X'}=\lim X'$, proportionality between image and reality $I'_j=X'/L_{X'}$, the position of the marker $Xj$.

On the Y axis we face a similar problem and for the same motion we have the following system of equations:

$Y'=\cos(\theta)(-(H+dZ)\tan(\theta)+X_0+dX)$, new real $Y$ coordinate

A similar reasoning can be applied in three dimensions. We consider the three dimension coordinate system (x,y,z) of the OR. We work with 3 translations and 3 rotations. As we know the equations of our problem we had: to simulate, for each point, its new position with respect to each possible set of parameters, and then minimize the quadratric distance between the real observation and the simulation. We wrote with a matlab code a simulator based on a cross motif. This code applies successively each transformation to the image viewed from the trocar.

Figure 17:
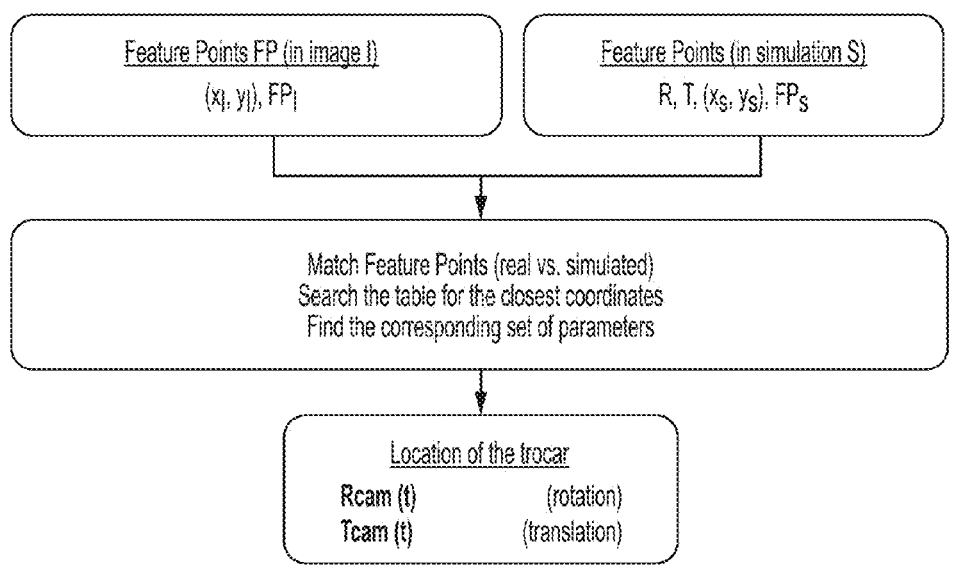
FIG. 17 is a triangulation algorithm of exemplary embodiments.

In order to solve our localization problem we put in place a method that needs to be accurate and fast. Our idea to achieve the simulation of the feature points' new position is to first simulate all the possible positions of the feature points within the room for any set of parameters. With each set the idea is to compute from the coordinates of the feature points in the first of the two images, their new position in the second image and then to compare it to the coordinates of the feature points we really observe in this second image. With this comparison we will have to minimize an error criterion. This way we would be able to save intraoperative computation time. Our algorithm works as described on the scheme shown in FIG. 17.

Figure 18:
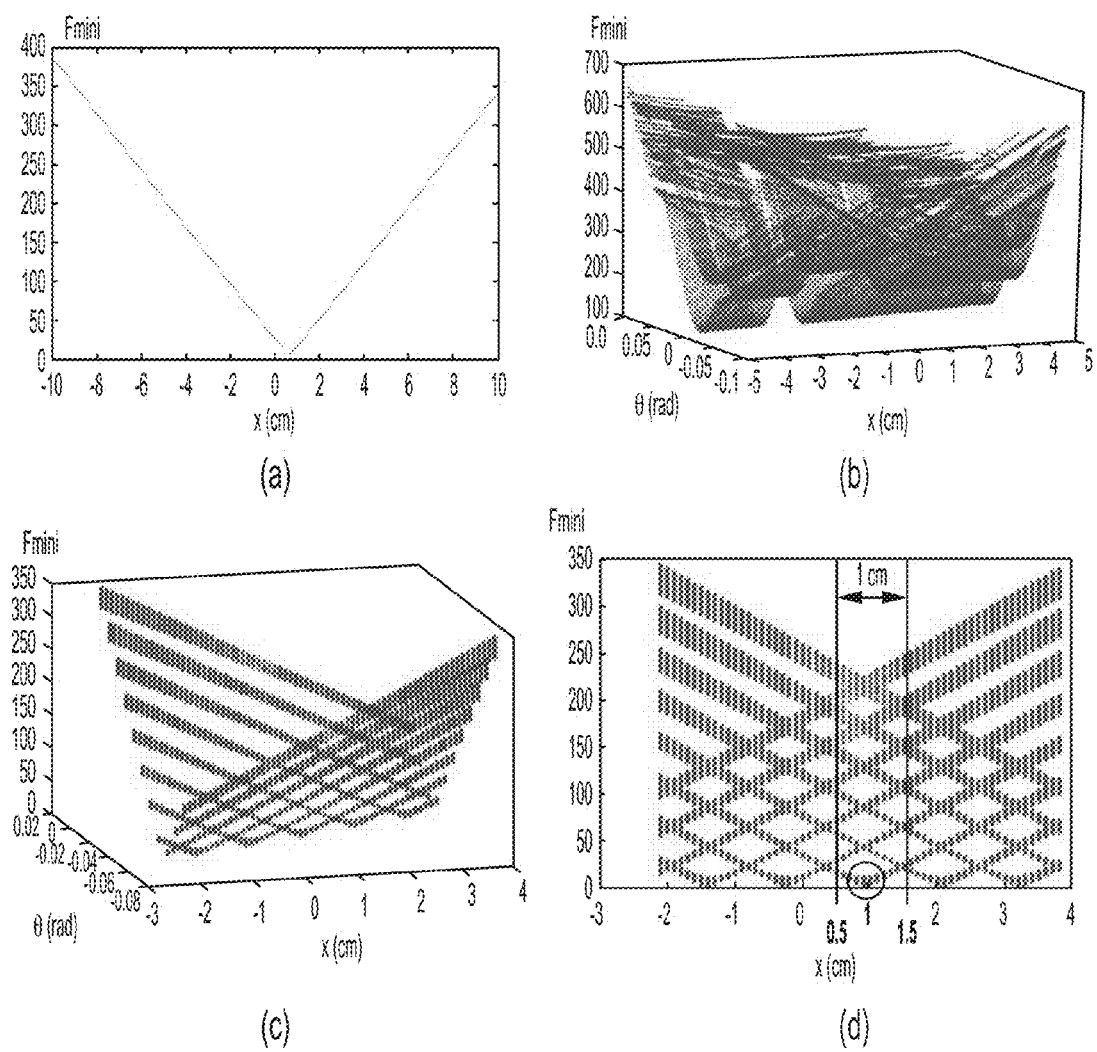
FIG. 18 is a graphical representation of minimized functions of exemplary embodiments.

The first results on only one degree of displacement were very encouraging—see graph (a) of FIG. 18. However, there was a problem as soon as we tried to estimate the parameters for a motion with more than one degree of freedom. Indeed, there were too many chances to be stuck in local minimum instead of the global minimum of the error function—see graph (b) of FIG. 18. A paper written by Yuan ("A general photogrammetric method for determining object position and orientation, IEEE Transactions on Robotics and Automation, Volume 5, Issue 2, pp 129-142, April 1989) provided guidance. In order to solve the exterior calibration problem of a single camera we needed to use 4 non-colinear points to solve the system with existence and uniqueness of the solution. But even with this, our algorithm was presenting some local minimum and was too slow—see graph (c) of FIG. 18. Probably the hypothesis of considering a pinhole camera of Yuan's paper is too restrictive. At this moment we had to find another idea to solve our problem. It is at this point that we entered in a dynamic problem and not anymore a static one. Indeed, at the end what we want is to analyze videos. In a video two successive images are linked, which means that we can use the parameters found in the images n−1 to compute the one of the image n. By implementing that and by putting a limitation on the movement of the trocar between two images we achieve to finally have a unique minimum—see graph (d) of FIG. 18. This implies a limitation on the surgeons movements between two images of ±0.5 cm for the translations and ±4° for the rotations. And because the camera takes an average of 20 images per second and the movement of a surgeon is not suppose to be very fast we should never reach this limitation.

FIG. 18 provides a representation of our minimized function in function of different parameters and in different conditions. Graph (a) of FIG. 18 represents the case when we work in one dimension and four feature points. The minimum exists and is unique. Graph (b) of FIG. 18 represents what happens when we pass to a three dimensions problem. Every parameter of freedom bring his level of complexity. Looking for the targeted minimum take too much time and is not robust. Graph (c) of FIG. 18 represents our minimized function when we apply the consideration of Yuan's paper. There is less complexity but still a lot of local minimum. Graph (d) of FIG. 18 represents the function in our case which means with the limitation of movement between two images. On this 3 dimension plot you can see the results on a two dimensions representation. The circle represents the unique minimum when you restrain the region of interest to 1 centimeters of width.

However the trocar localization systems do not give us enough information to compute the exact position and orientation of the surgical tool. Indeed, in the trocar the laparoscopic instrument has a little margin that enables it to move in and out of the trocar, but it also causes an additional problem as it allows the tool not to have the exact same orientation as the trocar. Moreover the position of the trocar does not indicate the depth at which the tip of the tool is within the patient body. We have to deal with this issue in a second time.

Pattern Recognition

Both parts of the smart trocar, the localization and the recognition, need an identification algorithm to extract useful information from videos. For the GPS we need to detect the crosses on the ceiling. To achieve this we are applying morphological filtering and thresholding. Using prior knowledge about the markers shapes we are able to extract the feature points that we need. Here are the procedure of the extraction of the feature point—see FIG. 19(1) we detect the corner and take the ones that are useful (red dots), compute the middle of each (green dots), then FIG. 19(2) thanks to the knowledge of the position of the crosses between each other we are able to add the orientation of each point, i.e. if it is up of the cross (green), down (red), right (cyan) and left (yellow). At the end, for the computation of the position we only need four points FIG. 19(3). There exists multiple ways to choose these four points and we are still analyzing and trying to understand their role on the final accuracy.

Figure 19:
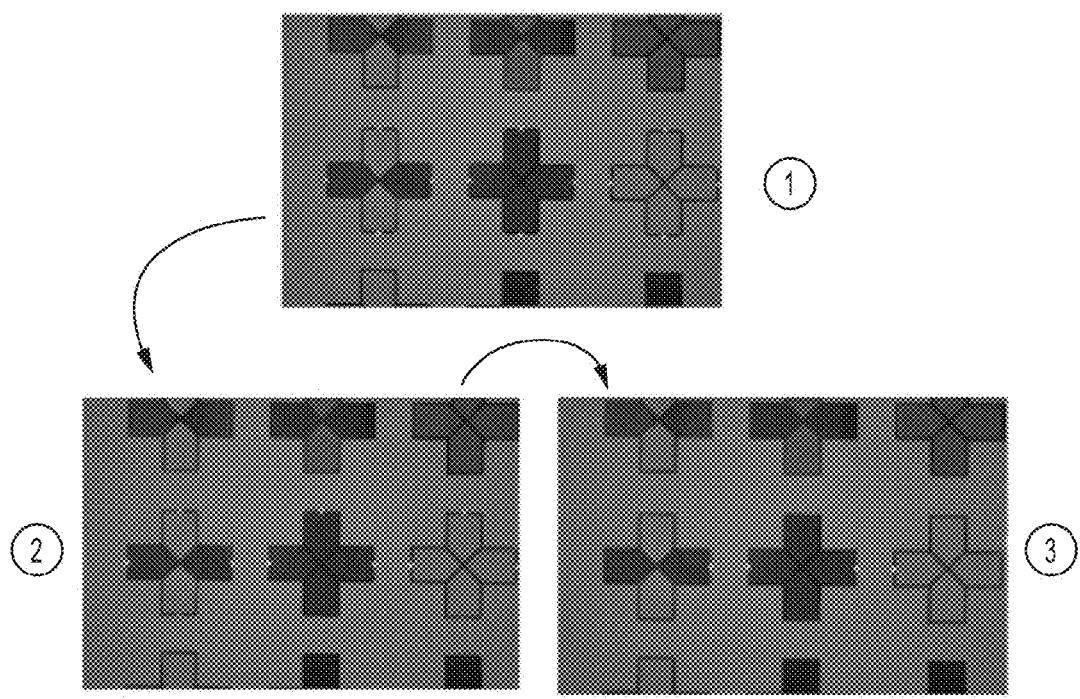
FIG. 19 shows results of the identification of landmarks on a ceiling according to exemplary embodiments.

FIG. 19 shows results of the identification part with picture of crosses on the ceiling of the OR taken with a professional camera. Eventually rotation of the tool can be easily registered from the color circle marker's—placed on the tool—rotation itself. We can then extract the position of the laparoscopic tool in the coordinate system attached to the trocar as follows. If the tool axis is perfectly aligned to the port axis, the distance from the marker to the port can be computed from the apparent diameter of the marker in the video stream. If this is not the case, the marker appears as an ellipse, instead of a disk, in the video stream. The axis of its small diameter and the axis of the tool gives the plan of the rotation. The ratio of the large diameter to the smallest diameter of the ellipse gives the angle $\alpha$ with a simple trigonometric formula. We should notice in practice that a is a small: a standard port has a 5 inches tubular guide, and a mismatch of 2 mm in diameter with the laparoscopic tool result in a maximum angle of 1°.

Results

The accuracy in this part of the project is very important. Precision for a surgeon is the key of a good surgery. The detection of the feature points has to be as accurate as possible to get the best matching between the points that we found in the image and the ones coming from the simulator. As seen before, the algorithm is dynamic that is to say that we are using previous knowledge at each steps of the algorithm. After a lot of tests on picture took with a professional camera we figured out that it is important that the movement between two images do not exceed a certain value. This allows us to restrain the number of possible movement in the next image and to have a faster algorithm. Indeed, we are trying to minimize a function, the distance between the coordinates of the feature points coming from the simulator and the ones found during the surgery. As seen before, we based our algorithm on the result of Yuan [6] who proved that we need 4 points to have a unique minimum. But the hypotheses of this paper are very restrictive and as our problem has six degrees of freedom, we end up with a lot of local minimum instead of a unique one. Fortunately, we found that on shorter region of interest of our six parameters there was a unique minimum as seen in the state of the art. To sum things up, for a movement between two images of less than ±0.5 cm in translation and less than ±4° in rotation we can meet the requirements imposed: 1 mm for the shift accuracy and 0.5° for the angle accuracy.

Identification of Rotation and Translation Values

Figure 20:
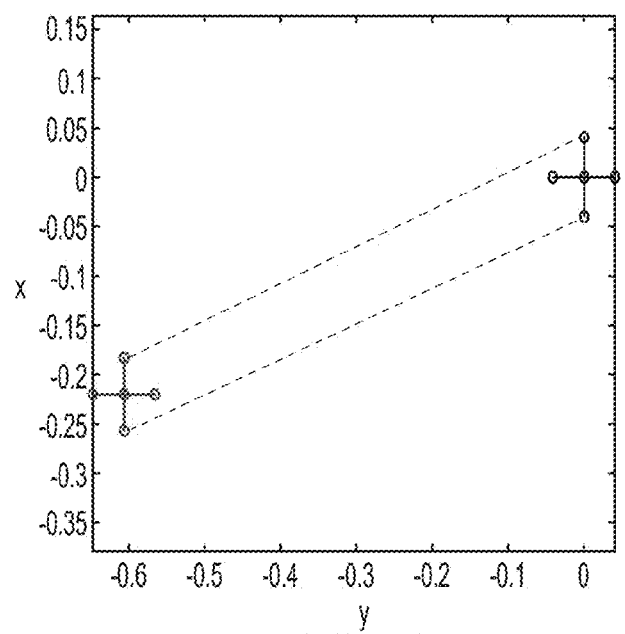
FIG. 20 shows the trajectory of landmarks according to exemplary embodiments.
Figure 22:
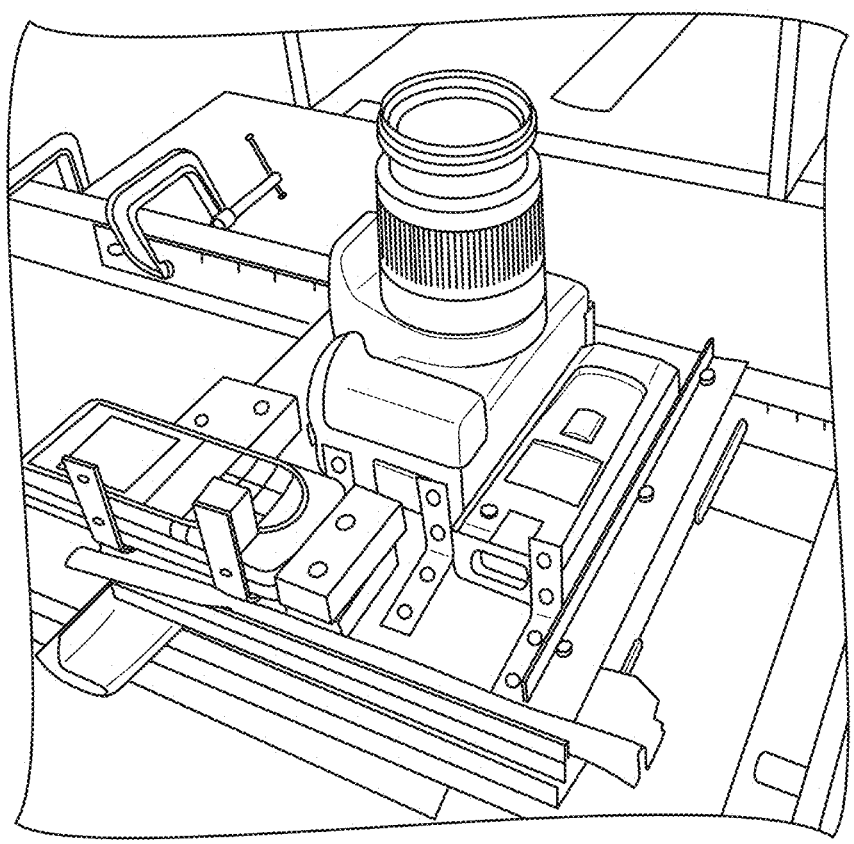
FIG. 22 is a photograph of equipment used for validation of data according to exemplary embodiments.

Let us see how we track back the movement of the trocar having a rotation component and a translation one. FIGS. 20 and 22 show a rapid prototyping to check that result. FIG. 20 shows a trajectory of the cross Landmark (from upper right to bottom left) with H=2; dx=−0.1; dy=0; dz=−0.3; θ=10°; Φ=20°.

We set first the camera in the flat position, and measure on the wall the height of the laser beam projection. We shoot in that position an image of the ceiling. The auto focus option of the camera was turned off. We set second the camera in a position that forms a small angle and translation with the desk. We measure on the wall the new position of the laser beam projection. From these two measures on the wall, we get the angle α with an accuracy of about 0.05°. We shoot in that new position an image of the ceiling. We observe indeed the displacement of the markers due to the change of orientation of the camera. We apply then our algorithm to reconstruct the rotation and the translation from these two images. We repeat this multiple times with different values of movement. The results are reported in the table in FIG. 21, showing the result of the experiment on two translations (in cm) and two rotations (in degrees). We did this experiment several times, and observe a good reliability of the method. Except for very large displacement, we keep the accuracy of order 1 mm. Finally we notice that horizontal displacement are much easier to monitor than vertical displacement. We are planning to check that we can keep this excellent level of accuracy in general conditions with a wireless camera. The first step is to correct the optic of this camera that has indeed a small "fish eye" effect. This is in principle standard procedure in digital photography.

The simulator helped us to compute the sensitivity of the system. Let us assume that the image comes with a resolution of 500 pixels in each dimension. This means that an accumulated error of 4 pixels in each spatial directions will results in an error of about 1 mm at the end of the laparoscopic tool real position. This error is very small indeed because the relative distance from the trocar to the ceiling is much larger than from the the trocar to the ROI inside the abdominal cavity. But this error can be quickly reached with a non robust feature points detection.

Validation

To develop new software that surgeons are going to use during procedure, the validation part of the project is an important one and it involves a lot of time. Compared to the validation of the tools recognition the validation of the localization part is more complicated. Indeed, the requirements are very precise. We want an accuracy of less than 1 mm and less than 0.5°. This means that, during the tests, you need to move your camera and be able to measure this displacement with at least 1 mm of accuracy too. We built a system in order to do this validation as shown in FIG. 23. It is composed by a three wood plates bounded by hinges that gives the whole plates system two degrees of freedom by providing them two axis of rotation. On the top of those plates we attached a digital camera, so that it looks to the ceiling, and two lasers each of them parallel to one of the rotation axis. You can see on the photo below our system. These two lasers plus other features allow us to have very accurate measures that we can use to compare with the output of the software.

* * *

While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

REFERENCES

The contents of the following references are incorporated by reference herein:

U.S. Provisional Patent Application 61/734,506.

WO 2014/089439.

3D IRCAD Liver Data Base http://www.ircad.fr/softwares/3Dircadb/3Dircadb1/?lng=en Agarwal S, Joshi A, Finin T, Yesha Y 2007). A Pervasive Computing System for the Operating Room of the Future. *Mobile Networks and Applications;* 12:215-28.

Aggarwal R, Moorthy K, and Darzi A (2004). Laparoscopic skills training and assessment. *Br J Surg; Vol.* 91, No. 12, pp. 1549-58.

Allan M, Ourselin S, Thompson S, Hawkes D J, Kelly J and Stoyanov D (2013). Toward detection and localization of instruments in minimally invasive surgery. *Biomedical Engineering. IEEE Transactions*; Vol. 60, No. 4, pp. 1050-1058.

Asano, T K, Soto, C, Poulin E C, Mamazza J, and Boushey R P (2011). Assessing the impact of a 2-day laparoscopic intestinal workshop. *Can J Surg*, 4, pp. 223-6.

Bano J, Hostettler A, Nicolau S, Cotin S, Doignon C, Wu H S, Huang M H, Soler L, Marescaux J (2012). Simulation of Pneumoperitoneum for Laparoscopic Surgery Planning *MICCAI*; Vol. 7510, pp. 91-98.

Bardram J E, Doryab A, Jensen R M, Lange P M, Nielsen K L G, and Petersen S T (2011). Phase recognition during surgical procedures using embedded and body-worn sensors. *PerCom*; pp. 45-53.

Blasinski H, Nishikawa A, and Miyazaki F (2007). The application of adaptive filters for motion prediction in visually tracked laparoscopic surgery. *Robotics and Biomimetics, ROBIO* 2007; *IEEE International Conference*; pp. 360-365.

Blum T, Padoy N, Feussner H, and Navab N (2008). Modeling and online recognition of surgical phases using Hidden Markov Models. *Med Image Comput Comput Assist Interv*; 11:627-35.

Blum T, Padoy N, Feussner H, Navab N. (2008). Modeling and online recognition of surgical phases using Hidden Markov Models. *Med Image Comput Comput Assist Interv;* 11:627-35.

Breedveld P, Stassen H, Meijer D W, and Jakimowicz J J (2000). Observation in laparoscopic surgery: overview of impeding effects and supporting aids. *J Laparoendosc Adv Surg Tech*; Vol. 10, No. 5, pp. 231-41.

Bucholz R D, Yeh D D, Trobaugh J, McDurmott L L, Sturm C D, Baumann C, Henderson J M, Levy A, and Kessman P. (1997). The correction of stereotactic inaccuracy caused by brain shift using an intraoperative ultrasound device. *Lecture Notes in Computer Science (MICCAI)*; Vol. 1205, No. 1997, pp. 459-66.

Carter T J, Sermesant M, Cash D M, Barratt D C, Tanner C, and Hawkes D J (2005). Application of soft tissue modelling to image-guided surgery. *Med Eng Phys*; Vol. 27, No. 10, pp. 893-909.

Climent J and Mares P. (2003). Real-time tracking system for assisted surgical operations. *Latin America Transactions, IEEE (Revista IEEE America Latina)*; 1(1):8-14.

Colombo, J R, Haber, G P Jr, Rubinstein M, and Gill I S (2006). Laparoscopic surgery in urological oncology: brief overview. *Int Braz J Urol*; 32(5):504-12.

Doryab A, and Bardram J E (2011). Designing activity-aware recommender systems for operating rooms. *Proceedings of the Workshop on Context-awareness in Retrieval and Recommendation*, pp; 43-6.

Doryab A, Togelius J, and Bardram J (2012). Activity-aware recommendation for collaborative work in operating rooms. *Proceedings of the ACM international conference on Intelligent User Interfaces*; pp. 301-4.

Dutkiewicz P, Kielczewski M, and Kowalski M. (2004). Visual tracking of surgical tools for laparoscopic surgery. *Robot Motion and Control, 2004. RoMoCo '04. Proceedings of the Fourth International Workshop*; pp. 23-28.

Dutkiewicz P, Kietczewski M, Kowalski M, and Wroblewski W (2005). Experimental verification of visual tracking of surgical tools. *Robot Motion and Control, RoMoCo '05. Proceedings of the Fifth International Workshop*; pp. 237-242.

Estebanez B, del Saz-Orozco Rivas P I, Bauzano E, Muoz V F and Garcia-Morales I, (2012). Maneuvers recognition in laparoscopic surgery: Artificial Neural Network and hidden Markov model approaches. *4th IEEE RAS & EMBS International Conference on Biomedical Robotics and Biomechatronics*; pp. 1164-1169.

Fasquel J, Brocker G, Moreau J, Agnus V, Papier N, Koehl C, Soler L, and Marescaux J (2006). A Modular and Evolutive Software for Patient Modeling Using Components, Design Patterns and a Formal XML-Based Component Management System. *CBMSm* $19^{th}$ *IEEE International Symposium*; pp. 43-50.

Franco D, (2001), Right hepatectomy, WeBSurg.com; 1(12).

Garbey, M, Salmon R, Thanoon D, Bass B (2013). Multiscale Modeling and Distributed Computing to Predict Cosmesis Outcome After a Lumpectomy. *J. Comput. Physics;* 244: 321-335.

Gould J, and Frydman J (2007). Reverse-alignment surgical skills assessment. *Surgical Endoscopy*; Vol. 21, No. 4, pp. 669-671.

Hawkes D J, Barratt D, Blackall J M, Chan C, Edwards P J, Rhode K, Penney G P, McClelland J and Hill D L G. (2005). Tissue deformation and shape models in image-guided interventions: a discussion paper. *Medical Image Analysis*; Vol. 9, No. 2, pp. 163-75.

Herron D, Gagner M, Kenyon T, and Swanström, L (2001). The minimally invasive surgical suite enters the 21st century. *Surgical Endoscopy*; Vol. 15, No. 4, pp. 415-422.

Hodgson A J, Pantazopol, R A, Visser, M D, Salcudean, S E, and Nagy, A G, (1997). "Assessing potential benefits of enhanced dexterity in laparoscopic surgery." *Engineering in Medicine and Biology Society. Proceedings of the* $19^{th}$ *Annual International Conference of the IEEE*; Vol. 5, pp. 1966-1969.

Ikuta K, Kato T, Ooe H, and Ando S. (2007). Surgery recorder system for recording position and force of forceps during laparoscopic surgery. *Advanced intelligent mechatronics, 2007 IEEE/ASME international conference*; pp. 1-6.

Jakimowicz J J, and Ruers T J M (1991). Ultrasound-Assisted Laparoscopic Cholecystectomy: Preliminary Experience. *Dig Surg*; Vol. 8(2), pp. 114-17.

Jakimowicz J J. (2006). Intraoperative ultrasonography in open and laparoscopic abdominal surgery: an overview. *Surg Endosc*, Vol. 20 Suppl 2, pp. S425-35.

Konishi K, Nakamoto M, Kakeji Y, Tanoue K, Kawanaka H, Yamaguchi S, Ieiri S, Sato Y, Maehara Y, Tamura S, and Hashizume M. (2007). A real-time navigation system for laparoscopic surgery based on three-dimensional ultrasound using magneto-optic hybrid tracking configuration. *IJCARS*; Vol. 2, No. 1, pp. 1-10.

Kranzfelder M, Schneider A, Blahusch G, Schaaf H, and Feussner H (2009). Feasibility of opto-electronic surgical instrument identification. *Minim Invasive Ther Allied Technol*; 18(5):253-8.

Kranzfelder M, Schneider A, Gillen S, and Feussner H (2011). New technologies for information retrieval to achieve situational awareness and higher patient safety in the surgical operating room: the MRI institutional approach and review of the literature. *Surg Endosc*; Vol. 25, No. 3, pp. 696-705

Kühnapfel U, çakmak H K, and Maass H. (2000). Endoscopic surgery training using virtual reality and deformable tissue simulation. *Computer & Graphics*, Vol. 24, No., pp. 671-82.

LangøT, Tangen G A, Mårvik R (2012). Navigated ultrasound in laparoscopic surgery. *Advances in Laparoscopic Surgery*; pp. 77-98.

Liu C C, Chang C H, Su M C, Chu H T, Hung S H, JWong J M, and Wang P C (2010). RFID-initiated workflow control to facilitate patient safety and utilization efficiency in operation theater. *Comput Methods Programs Biomed;* 3, pp. 435-42.

Liu C C, Chang C H, Su, M C, Chu H T, Hung S H, Wong J M and Wang P-C (2011). RFID-initiated workflow control to facilitate patient safety and utilization efficiency in operation theater. *Comput Methods Programs Biomed;* 104(3): 435-42.

Mackay S, Datta V, Chang A, Shah J, Kneebone R, and Darzi A (2003). Multiple Objective Measures of Skill (MOMS): a new approach to the assessment of technical ability in surgical trainees. *Ann Surg;* 2, pp. 291-300.

Mahmoud N, Nicolau S, Keshk A, Ahmad M A, Soler L, Marescaux J (2012). Fast 3D Structure From Motion with Missing Points from Registration of Partial Reconstructions. *AMDO*; pp. 73-183.

Marjamaa R, Vakkuri A, and KirvelÄ O (2008). Operating room management: why, how and by whom? *Acta Anaesthesiologica Scandinavica*; 52:596-600.

Mårvik R, Langø T, Tangen G A, Andersen J O, Kaspersen J H, Ystgaard B, Sjolie E, Fougner R, Fjøsne H E, and Hernes T A. (2004). Laparoscopic navigation pointer for 3-D image guided surgery. *Surg Endosc*; Vol. 18, No. 8, pp. 1242-8.

Nakamoto M, Hirayama H, Sato Y, Konishi K, Kakeji Y, Hashizume M, and Tamura S. (2007). Recovery of respiratory motion and deformation of the liver using laparoscopic freehand 3D ultrasound system. Medical Image Analysis; Vol. 11, No. 5, pp. 429-42.

Nakamoto M, Nakada K, Sato Y, Konishi K, Hashizume M, and Tamura S (2008). Intraoperative Magnetic Tracker Calibration Using a Magneto-Optic Hybrid Tracker for 3-D Ultrasound-Based Navigation in Laparoscopic Surgery. *Medical Imaging, IEEE Transactions;* 27(2):255-270.

Navarro A A, Hernansanz A, Villarraga E A, Giralt X, and Aranda J (2007). Enhancing Perception in Minimally Invasive Robotic Surgery through Self-Calibration of Surgical Instruments. *Engineering in Medicine and Biology Society, EMBS* 2007, *29th Annual International Conference of the IEEE*; pp. 457-460.

Neumuth D, Loebe F, Herre H, and Neumuth T (2011). Modeling surgical processes: a four-level translational approach. *Artif Intell Med. Netherlands;* 51(3):147-61.

Neumuth T, Jannin P, Schlomberg J, Meixensberger J, Wiedemann P, and Burgert O (2011). Analysis of surgical intervention populations using generic surgical process models. *Int J Comput Assist Radiol Surg;* 6:59-71.

Neumuth T, Jannin P, Strauss G, Meixensberger J, and Burgert O (2009). Validation of knowledge acquisition for surgical process models. *J Am Med Inform Assoc;* 16(1):72-80.

Neumuth T, Strauss G, Meixensberger J, Lemke H, and Burgert O (2006). Acquisition of Process Descriptions from Surgical Interventions. *Database and Expert Systems Applications*; pp. 602-11.

Nicolau S, Mendoza-Burgos L, Soler L, Mutter D, Marescaux J (2008). In Vivo Evaluation of a Guidance System for Computer Assisted Robotized Needle Insertion Devoted to Small Animals. *MIAR*; pp 241-250.

Padoy N, Blum T, Ahmadi S-A, Feussner H, Berger M-O, and Navab N (2012). Statistical modeling and recognition of surgical workflow. *Medical Image Analysis;* 16:632-41.

Payandeh S, Xiaoli Z, and Li A. (2001). Application of imaging to the laproscopic surgery. *Computational Intelligence in Robotics and Automation, Proceedings* 2001, *IEEE International Symposium*; pp. 432-437.

Reddy S K, Tsung A, Geller D A. (2010) Laparoscopic Liver Resection. *World Journal of Surgery;* 35:1478-1486.

Reinertsen I, Lindseth F, Unsgaard G, and Collins D L (2007). Clinical validation of vessel based registration for correction of brain-shift. *Medical Image Analysis;* 11(6): 673-84.

Richardson W, Stefanidis D, Mittal S, and Fanelli R D (2010). SAGES guidelines for the use of laparoscopic ultrasound. *Surg Endosc;* 24:745-56.

Sarker S K, Chang A., and Vincent C (2006). Technical and technological skills assessment in laparoscopic surgery. *JSLS*; Vol. 10, No. 3, pp 284-92.

Scheuering M, Schenk A, Schneider A, Preim B, and Greiner G. (2003). Intraoperative Augmented Reality for Minimally Invasive Liver Interventions. *Proc SPIE*; Vol. 5029, pp. 407-17.

Schoepp H. *Surgical Navigation System* (2012).

Shahidi R, Bax M R, Maurer C R Johnson J A, Wilkinson E P, Wang B, West, J B, Citardi M J, Manwaring K H and Khadem R (2002). Implementation, Calibration and Accuracy Testing of an Image Enhanced Endoscopy System. *IEEE Trans Med Imaging*; Vol. 21, No. 12, pp. 1524-35.

Society of American Gastrointestinal and Endoscopic Surgeons, http://www.sages.org/

Soler L, Nicolau S, Fasquel J, Agnu V, d Charnoz A, Hostettler A, Moreau J, Forest C, Mutter D, and Marescaux J (2008). Virtual reality and augmented reality applied to laparoscopic and notes procedures. *ISBI*; pp. 1399-1402.

Staub C, Lenz C, Panin G, Knoll A, and Bauernschmitt R (2010). Contour-based surgical instrument tracking supported by kinematic prediction. *Biomedical Robotics and Biomechatronics (BioRob)*, 2010 *3rd IEEE RAS and EMBS International Conference*; pp. 746-752.

Stoll J, Ren H and Dupont P E (2012). Passive Markers for Tracking Surgical Instruments in Real-Time 3-D Ultrasound Imaging. *IEEE Transactions on Medical Imaging*; Vol. 31, No. 3, pp. 563-575.

Tatar F, Mollinger J, Bossche A (2003). Ultrasound system for measuring position and orientation of laparoscopic surgery tools. *Sensors, Proceedings of IEEE*; Vol. 2, pp. 987-990.

Tatar F, Mollinger J R, Bastemeijer J, and Bossche A (2004). Time of flight technique used for measuring position and orientation of laparoscopic surgery tools. *Sensors,* 2004. *Proceedings of IEEE*, p. 1596.

Thanoon D, Garbey M. and Bass B L (2013). Deriving Indicators for Breast Conserving (BCS) using Finite Element Analysis (FEM). *Computer Methods in Biomechanics and Biomedical Engineering*; pp. 1-12.

Tsai C-C and Wang T-Y (2008). Small humanoid robot localization by landmarks. *7th World Congress on Intelligent Control and Automation*; pp. 6584-6589.

Uchida T, Koyama H, Komeda T, Miyagi M and Funakubo H (1996). Measuring method of three dimensional position and orientation of a moving object for medical robots, *IEEE International Conference on Systems, Man, and Cybernetics*; Vol. 2, pp. 887-892.

Unsgaard G, Rygh O M, Selbekk T, Müller T B, Kolstad F, Lindseth F, and Hernes T A. (2006). *Intra-operative 3D ultrasound in neurosurgery. Acta Neurochirurgica*; Vol. 148, No. 3, pp. 235-53.

Voros S, Orvain E, Cinquin P, and Long J A (2006). Automatic detection of instruments in laparoscopic images: a first step towards high level command of robotized endoscopic holders. *Biomedical Robotics and Biomechatronics, BioRob 2006. The First IEEE/RAS-EMBS International Conference*; pp. 1107-12.

Wein W, Khamene A, Clevert D-A, Kutter 0, Navab N (2007). Simulation and Fully Automatic Multimodal Registration of Medical Ultrasound. *Medical Image Computing and Computer-Assisted Intervention—MICCAI 2007, Lecture Notes in Computer Science*; Vol. 4791, pp. 136-14.

Wolpert S, Bosseau Murray W, Gorman P J, and Bholat O S (1999). Movement trajectories in laparoscopic tools. *Engineering in Medicine and Biology. 21st Annual Conf and the Annual Fall Meeting of the Biomedical Engineering Soc. BMES/EMBS Conference. Proceedings of the First Joint*; Vol. 2.

Wytyczak-Partyka A, Nikodem J, Klempous R, Rozenblit J, Radoslaw Klempous, and Rudas I (2009). Safety Oriented Laparoscopic Surgery Training System. *Computer Aided Systems Theory—EUROCAST*; Vol. 5717, pp. 889-896.

Yuan J S-C (1989). A general photogrammetric method for determining object position and orientation. *IEEE Transactions on Robotics and Automation*; Vol. 5, Issue 2, pp. 129-142.

Zhu W, Nicolau S, Soler L, Hostettler A, Marescaux J, and Rémond Y (2012). Fast Segmentation of Abdominal Wall: Application to Sliding Effect Removal for Non-rigid Registration. *Abdominal Imaging*; pp. 198-207.

What is claimed is:

1. A surgical tool global positioning system comprising:
    a surgical port comprising a first axis, a proximal end configured to be located outside a body of a patient and a distal end configured to be located within an internal portion of the body of the patient, and a channel extending between the proximal end and the distal end;
    a first reference marker positioned at a first fixed location distal to the surgical port, wherein the first reference marker is positioned on a wall or a ceiling of an operating room;
    a tool inserted into the surgical port;
    a tracking element coupled to the tool inserted into the surgical port; and
    a camera coupled to the surgical port, wherein:
        the surgical port comprises a first axis;
        the tool comprises a second axis;
        the camera is coupled to the proximal end of the surgical port and is directed towards the first reference marker;
        the camera is configured to capture image data associated with the first reference marker;
        the camera is configured to detect image data associated with the tracking element coupled to the tool inserted into the surgical port;
        the image data associated with the first reference marker is used to determine a global position of the surgical port;
        the image data associated with the tracking element coupled to the tool inserted into the surgical port is used to determine an angle α between the first axis of the surgical port and the second axis of the tool;
        the image data associated with the tracking element coupled to the tool inserted into the surgical port is used to determine the distance between the tracking element and the surgical port;
        the image data associated with the first reference marker, the angle α between the first axis of the surgical port and the second axis of the tool, and the distance between the tracking element and the surgical port are used to determine a global position of the tool inserted into the surgical port.

2. The system of claim 1, wherein the first reference marker comprises a plurality of intersecting segments.

3. The system of claim 2, wherein the plurality of intersecting segments forms a cross shape.

4. The system of claim 1 wherein further comprising a second reference marker positioned at a second fixed location distal to the surgical port.

5. The system of claim 1, wherein the surgical port is a trocar.

6. The system of claim 5, wherein the trocar comprises a base at the proximal end and a cannula at the distal end, and wherein the camera is mounted to the base.

7. The system of claim 1, wherein the camera is in a fixed position with respect to the surgical port.

8. The system of claim 1, wherein the camera is configured to be directed away from a body of a patient.

9. The system of claim 1, wherein the camera includes a light element for illuminating the first reference marker.

10. The system of claim 1, further comprising a computer system, wherein the camera is in communication with the computer system to transmit the image data to the computer system.

11. The system of claim 1, wherein the tracking element includes at least one of a color, a shape, a pattern, bar code, and a character.

12. The system of claim 1 wherein:
    the surgical tool is sized and configured to access the internal portion of the body of the patient through the channel of the surgical port.

13. The system of claim 1, wherein the tracking element corresponds to at least one of an identity of the surgical tool, an orientation of the surgical tool, and a position of the surgical tool.

14. The surgical tracking system of claim 1, wherein the tracking element is positioned at a location proximate a handle associated with the surgical tool.

15. The system of claim 1, wherein the camera is further configured to capture image data associated with a surgeon.

* * * * *